(12) United States Patent
Sokol et al.

(10) Patent No.: US 7,770,454 B2
(45) Date of Patent: Aug. 10, 2010

(54) LASER SYSTEM AND METHOD FOR NON-DESTRUCTIVE BOND DETECTION AND EVALUATION

(75) Inventors: David W. Sokol, Dublin, OH (US); Craig T. Walters, Powell, OH (US); Jeff L. Dulaney, Delaware, OH (US); Steven M. Toller, Dublin, OH (US)

(73) Assignee: LSP Technologies, Inc., Dublin, OH (US)

( * ) Notice: Subject to any disclaimer, the term of this patent is extended or adjusted under 35 U.S.C. 154(b) by 221 days.

(21) Appl. No.: 10/950,865

(22) Filed: Sep. 27, 2004

(65) Prior Publication Data

US 2005/0120803 A1 Jun. 9, 2005

Related U.S. Application Data

(60) Provisional application No. 60/507,076, filed on Sep. 26, 2003.

(51) Int. Cl.
*G01N 29/04* (2006.01)

(52) U.S. Cl. .............................. 73/588; 73/801; 73/842

(58) Field of Classification Search .................. 73/587, 73/588, 590, 801, 842, 844, 845, 778–788, 73/815, 827; 381/396; 219/121.61, 121.85, 219/121.62, 121.64; 372/38.02, 38.07
See application file for complete search history.

(56) References Cited

U.S. PATENT DOCUMENTS

| | | | | |
|---|---|---|---|---|
| 4,004,456 A | * | 1/1977 | Vahaviolos | 73/801 |
| 4,090,400 A | * | 5/1978 | Vahaviolos | 73/801 |
| 4,207,771 A | * | 6/1980 | Carlos et al. | 73/587 |
| 4,401,477 A | * | 8/1983 | Clauer et al. | 148/525 |
| 4,545,018 A | * | 10/1985 | Clements et al. | 700/166 |
| 4,901,357 A | * | 2/1990 | Albright | 381/400 |
| 5,127,019 A | * | 6/1992 | Epstein et al. | 372/108 |
| 5,269,778 A | * | 12/1993 | Rink et al. | 606/12 |
| 5,473,315 A | * | 12/1995 | Holroyd | 340/683 |
| 5,572,016 A | * | 11/1996 | Wood et al. | 250/227.15 |
| 5,729,012 A | * | 3/1998 | Wood et al. | 250/227.15 |
| 5,803,965 A | * | 9/1998 | Yoon | 117/4 |
| 5,965,877 A | * | 10/1999 | Wood et al. | 250/227.15 |
| 6,008,887 A | * | 12/1999 | Klein et al. | 356/28.5 |
| 6,238,187 B1 | * | 5/2001 | Dulaney et al. | 416/241 R |
| 6,282,964 B1 | * | 9/2001 | Hancock et al. | 73/622 |
| 6,288,358 B1 | * | 9/2001 | Dulaney et al. | 219/121.6 |

(Continued)

FOREIGN PATENT DOCUMENTS

GB 2225427 A * 3/1990

*Primary Examiner*—J M Saint Surin
(74) *Attorney, Agent, or Firm*—Benjamen E. Kern

(57) ABSTRACT

A system for evaluating the integrity of a bonded joint in an article includes a laser configured in a laser shock processing arrangement to perform a laser shock processing treatment on the article. A beam delivery system employs an articulated arm assembly to communicate the radiant energy emitted by the laser to a process head proximate the article. The laser shock processing treatment causes the formation of shockwaves that propagate through the article, inducing internal stress wave activity that characteristically interacts with the bonded joint. A sensor detects a stress wave signature emanating from the article, which is indicative of the integrity of the bond. A detector such as a non-contact electromagnetic acoustic transducer provides a measure of the stress wave signature in the form of surface motion measurements.

20 Claims, 16 Drawing Sheets

U.S. PATENT DOCUMENTS

| | | | |
|---|---|---|---|
| 6,373,876 B1 * | 4/2002 | Dulaney et al. | 372/98 |
| 6,512,584 B1 * | 1/2003 | O'Loughlin et al. | 356/388 |
| 6,554,921 B2 * | 4/2003 | Sokol et al. | 148/508 |
| 6,759,626 B2 * | 7/2004 | Clauer et al. | 219/121.6 |
| 6,848,321 B2 | 2/2005 | Bossi et al. | |
| 6,945,114 B2 * | 9/2005 | Kenderian et al. | 73/643 |

* cited by examiner

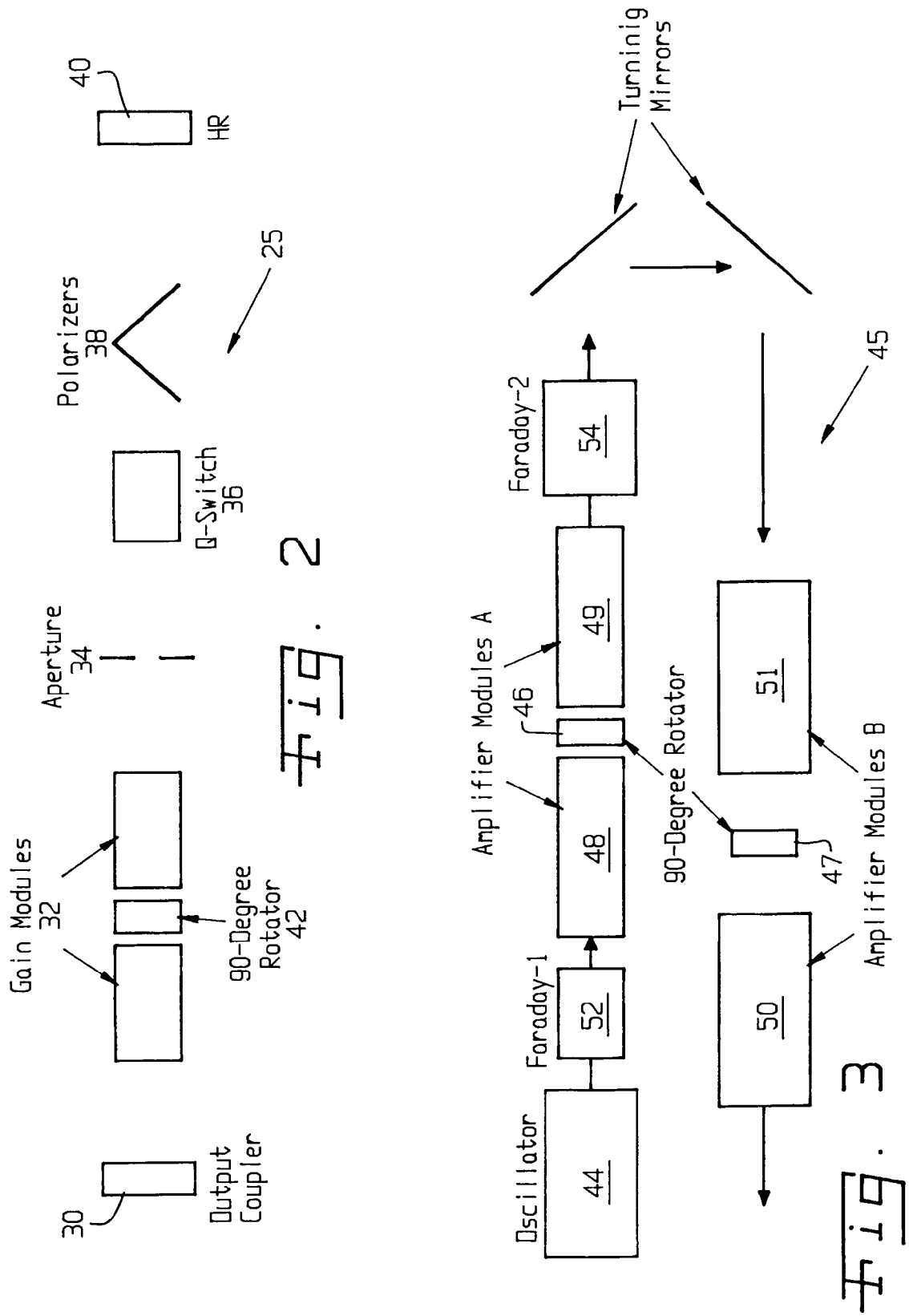

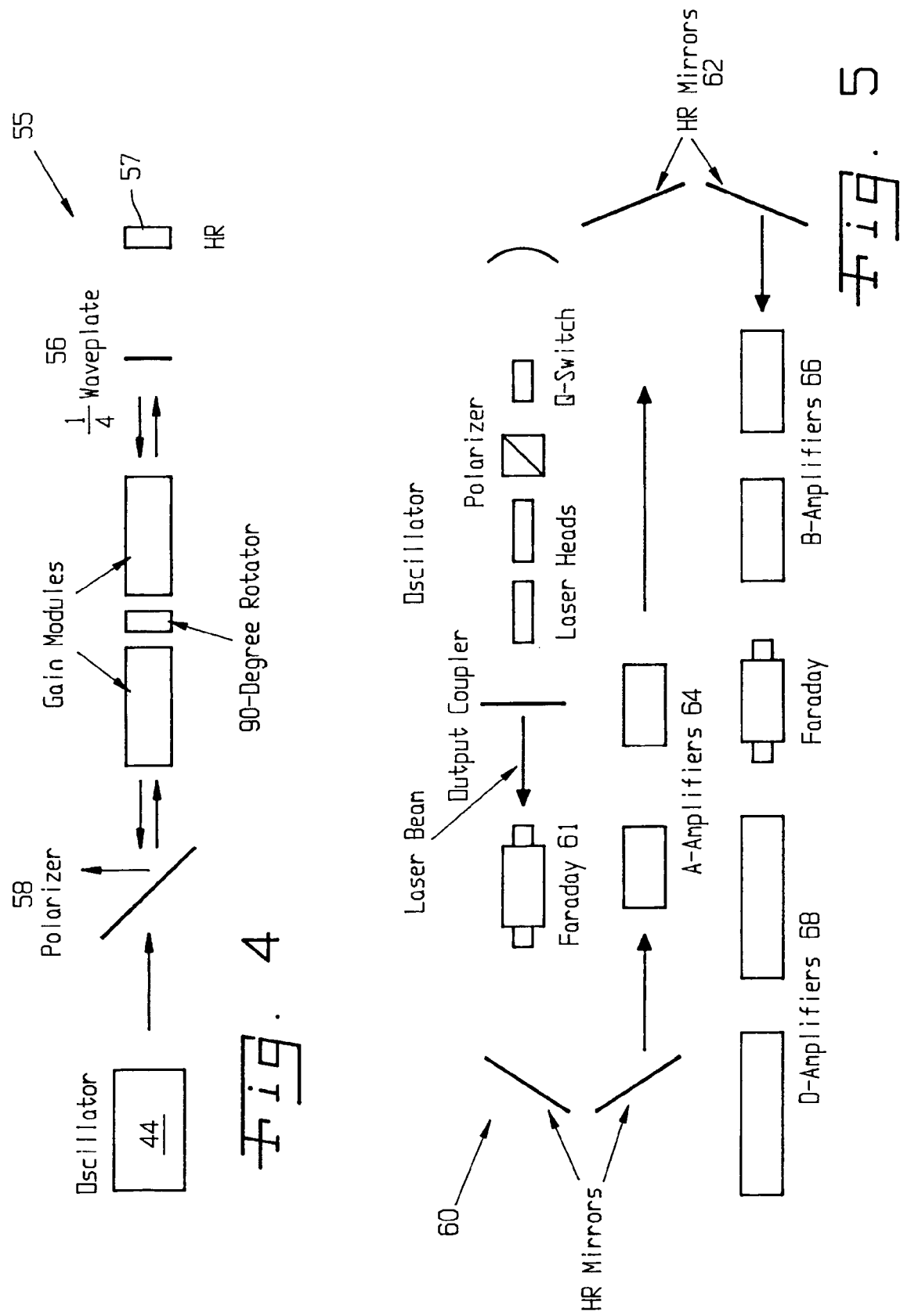

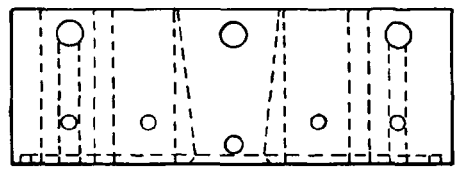
Fig. 8C
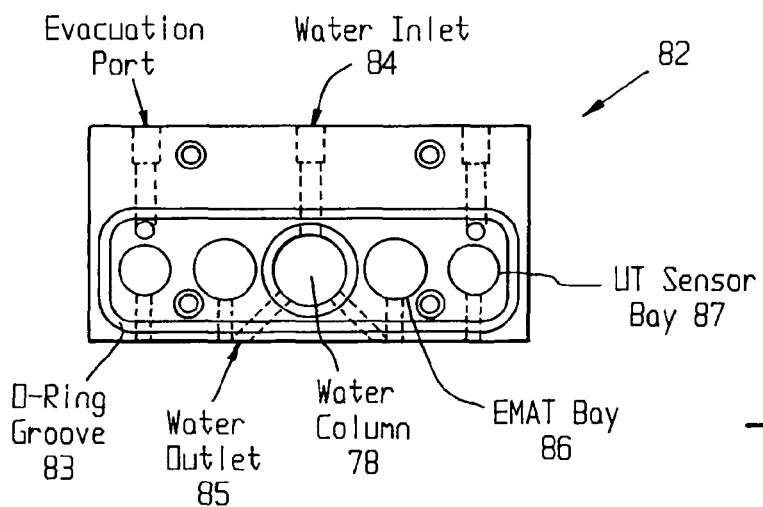
Fig. 8A
Fig. 8B

LASER SYSTEM AND METHOD FOR NON-DESTRUCTIVE BOND DETECTION AND EVALUATION

CROSS-REFERENCE TO RELATED APPLICATIONS

This application claims the benefit of prior filed U.S. Provisional Application No. 60/507,076 entitled LASER SYSTEM AND METHOD FOR NON-DESTRUCTIVE BOND DETECTION AND EVALUATION filed Sep. 26, 2003, in the name of the above named inventors, the disclosure of which is incorporated herein by reference thereto.

BACKGROUND OF THE INVENTION

1. Field of the Invention

The present invention relates to method and apparatus for preferentially testing the strength of composite bonds, and, more particularly, to the use of laser-induced shockwaves for conducting proof-testing of bonded joints in composite assemblies employing a non-destructive evaluation (NDE) and non-destructive inspection (NDI) strategy.

2. Description of the Related Art

An important task in the aircraft industry is the non-destructive inspection (NDI) of composite structures assembled with adhesive bonds. In particular, it is of interest to find weakly bonded layers in multi-layer carbon-fiber/resin-matrix skins and internal members. These weak bond areas typically are not observable with conventional ultrasound or thermal techniques because the bond between layers, while weak, is intact or in contact and no delamination area exists that would be visible to standard inspection techniques. These defective bonds could arise from improper preparation of the surfaces to be bonded, improper mixing, application, and/or curing of the adhesive, or contamination of the surfaces before bonding.

Previously, electron beam pulses have been used to deposit energy in depth in a composite structure on a time scale that is short compared to the acoustic transit time through the thickness of the material. This energy deposition results in a release wave propagating into the material from both surfaces. When the release waves meet they produce a tensile stress which can be used to test the strength of the bond at that point in the material. However, the electron beam generator is massive, therefore not portable, and the output beam cannot be conveniently moved around the surface of the aircraft to test the skin or other structural members.

SUMMARY OF THE INVENTION

According to the present invention there is provided in one form a means to inspect and evaluate bonded joint structures by inducing a laser-generated shockwave that propagates through the article under inspection and consequently produces a compression and/or tension state in the article. The shockwave imparted to the article is correlated with an associated vibration signature that contains information signifying the integrity of the bonded joint. Exemplary data such as front-surface and back-surface particle velocity signature measurements provide indicia of the integrity of the bond.

Various integrity analyses can be conducted to detect numerous article conditions and features, including, but not limited to, delamination, the presence or absence of a void at a certain interface (e.g., adhesion layer or laminate area), presence or absence of a defect or weakness (e.g., crack), a non-bond and non-contact condition, a non-bond but in-contact condition (e.g., a "kissing" interface), a partial bond condition, and a full bond condition. In one exemplary analysis, the shockwave is sufficient to create an appropriate stress capable of breaking a weak and malformed defective bond, yet not compromising other bond areas that are formed with the intended design strength.

The laser bond inspection and evaluation strategies may be applied to determine the dynamic strength of various structural entities, including, but not limited to, bonded composite structures, bonded structures having any material composition, and unbonded solid materials. The apparatus of the invention can be employed to detect specified conditions in any type of joint or bonding configuration, such as adhesive bonding and laminar arrangements.

The apparatus of the invention may be configured to provide remote flexible delivery of optical energy and to apply a localized targeted stress wave.

One advantage of the present invention is that a non-destructive evaluation and non-destruction inspection methodology has been developed.

Another advantage of the present invention is that the invention may employ a non-contact-type sensor to acquire the necessary stress wave signature data useful in identifying bond failure and bond condition.

A further advantage of the invention is that real-time evaluation of bond status and condition can be accomplished concurrently with collection of the stress wave signature data.

Another advantage of the invention is that the benefits of laser shock peening can be applied to the laser bond inspection process of the invention.

Another advantage of the invention is that a non-thermal loading mechanism can be employed to generate the shockwave activity needed to induce the stress waves in the article under study.

Another advantage of the invention is that various laser parameter values can be tailored to optimize acquisition of the stress wave signature data, such as pulse width, repetition rate, and energy level.

Another advantage of the invention is that the articulated arm assembly provides a highly flexible and maneuverable apparatus for selectively guiding the laser beam from a remote situs to difficult-to-access target locations, such as corners and bends not otherwise reached by line-of-sight communications.

Another advantage of the invention is that the laser pulse width can be variably chosen to accommodate the particular application environment, such as sensor technique, target material, and target location, and target geometry.

Another advantage of the invention is that significant cost savings are possible with the use of detectors such as electromagnetic acoustic transducers, without compromising efficiency or performance.

Another advantage of the invention is that various alternative laser oscillator configurations can be provided to enhance the laser bond inspection process.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 2 is a block diagram schematic view of an oscillator configuration for the laser subsystem of FIG. 1, according to another form of the invention;

FIG. 3 is a block diagram schematic view of an oscillator configuration for the laser subsystem of FIG. 1, according to another form of the invention;

FIG. 4 is a block diagram schematic view of an oscillator configuration for the laser subsystem of FIG. 1, according to another form of the invention;

FIG. 5 is a block diagram schematic view of an oscillator configuration for the laser subsystem of FIG. 1, according to another form of the invention;

FIGS. 8A-C illustrate various views of a faceplate design for use with the process head attachment of FIG. 7;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
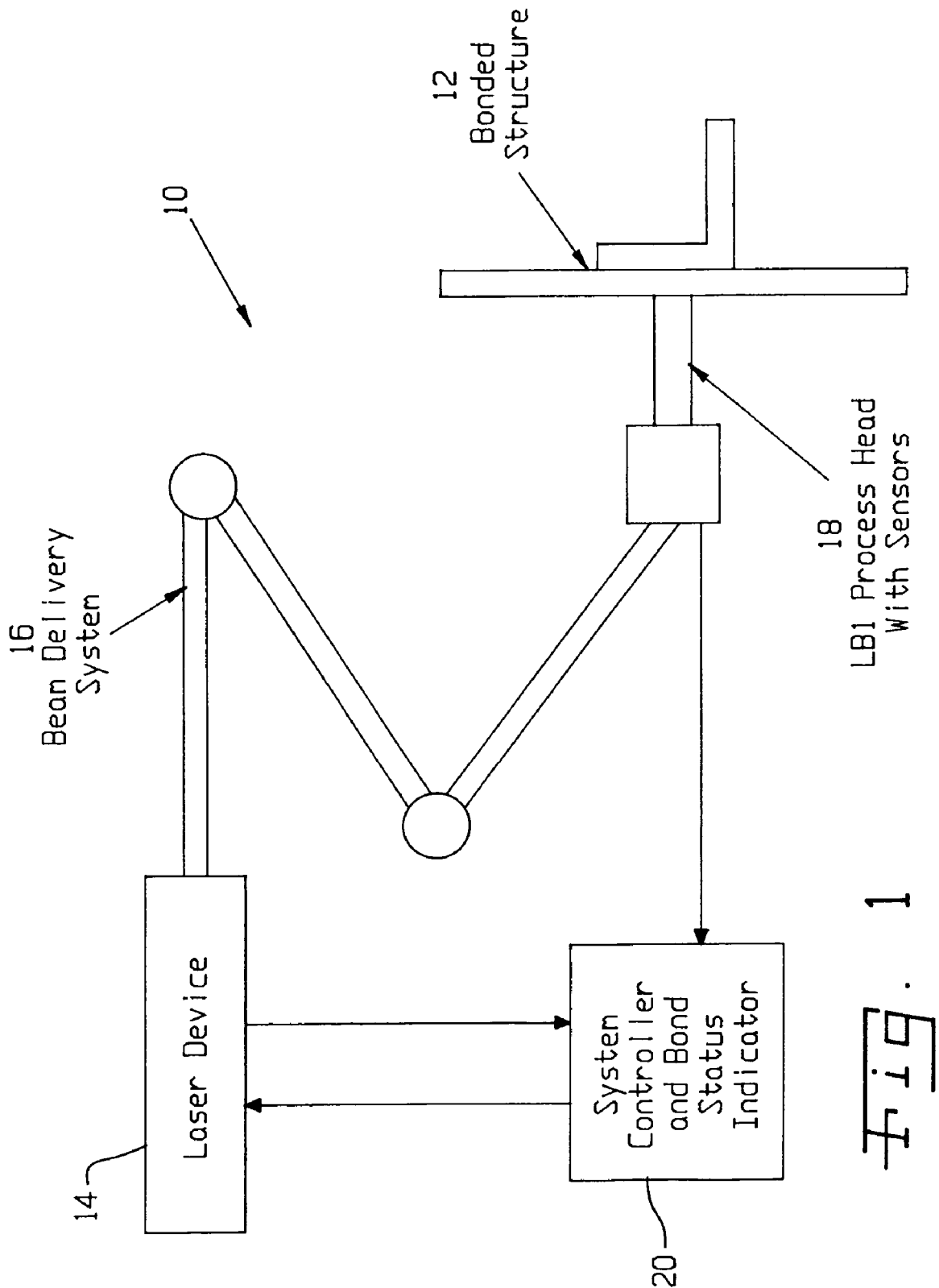
FIG. 1 is a block diagram schematic view of a laser bond inspection system, according to one form of the invention.

Referring now to the drawings and particularly to FIG. 1, there is shown a schematic block diagram illustration of a system 10 for evaluating the integrity of a bonded joint in a bonded structure or article 12, according to one form of the invention. As discussed further, system 10 includes a laser device 14 for emitting radiant energy; a beam delivery system (generally depicted at 16 in the exemplary form of an articulated arm assembly) for communicating the laser beam emissions to the target (i.e., article 12); a process head 18 providing an interface between the output of beam delivery system 16 and article 12, and further providing a sensor to collect measurement data from article 12; and a system manager provided in the form of processor-controller 20, which is configured to provide various control functions and to process and evaluate the data collected by the process head sensor, namely, stress wave signature data emanating from article 12.

The illustrated laser assembly 14 is preferably employed to generate a laser beam having a pulsed emission, according to one form of the invention. In general, the pulse width should have a width shorter than the width of the stress wave pulse desired for interrogating the structure of interest, namely, article 12.

It must be at least shorter than the transit time of a stress wave through the material thickness being inspected. For example, the transit time in a 9-mm thick carbon-fiber-reinforced epoxy composite might be 3 µs. Accordingly, in this example, the stress wave (and hence the laser pulse) must be less than 3 µs in order to develop a tensile wave upon reflection of the initial compressive wave from the back surface. A stress pulse width and laser pulse width of about 300 ns or less has been found to be useful for inspecting bonds in this type of material.

If the pulse width is too narrow (for, example 20 ns), the composite material or bond could be damaged by the compressive wave which would not give a good tensile strength indication. On the other hand, if only a short pulse laser is available, it has been found that wide stress pulses can be generated by including shock conditioning material on the front surface of the work piece being inspected. An appropriate thin layer of metal (for example spring steel or stainless steel with thickness in the 0.001 to 0.010 inch range) will cause an incident short stress pulse produced by a short laser pulse to reverberate in the metal layer and transmit a wide stress wave pulse because of the mismatch in acoustic impedance of the metal layer and the composite material. If the material to be inspected has a high sound speed, then short stress wave pulse widths may be need for laser bond inspection, for example, a 5-mm thick aluminum has a sound transit time of about 1 µs.

The wavelength of the laser may be any suitable wavelength that permits generation of a stress wave in the material under study, i.e., article 12. Particularly useful are solid-state lasers because they are reliable and compact. The pulse energy of the laser should be sufficient to provide a prescribed fluence over an area or areas with characteristic dimensions comparable to the thickness of the material being tested. The prescribed fluence must be of sufficient magnitude to produce the desired interrogating tensile stress in the material.

In one exemplary form, one set of illustrative laser parameters employs 1 to 100 J per pulse, 1 to 1000 ns pulse width, and 300 to 3000 nm wavelength. For example, the invention may be practiced with an Nd:glass laser (1054 nm wavelength), a 20-300 ns pulse width, and 3-50 J per pulse. The beam has a flat-top spatial profile and is circular in cross-section, however this should not be considered as limiting. However, these specifications should not be construed in limitation of the invention, as is should be apparent that other suitable laser parameter values may be chosen, according to the invention.

According to another form of the invention, the laser subsystem 14 can be provided in various oscillator arrangements.

As discussed further, FIGS. 2-5 illustrate in block diagram schematic form various exemplary oscillator configurations for laser subsystem 14.

Referring to FIG. 2, there is shown a laser oscillator arrangement according to a Master Oscillator Power Amplifier (MOPA) configuration 25. The laser device, for example, may be any suitable laser such as a pulsed Nd:phosphate glass device. Exemplary laser parameters may include temporal pulse and energy per pulse values selectable in the range of 20-400 ns and 10-100 Joules, respectively. Additionally, the laser can be configured to emit one or more laser beams, depending upon the desired stress wave activity for article 12.

The laser oscillator arrangement 25 used in the MOPA system depicted in FIG. 2 includes an output coupler 30, one or more gain modules 32, a mode control aperture 34 (for TEM 00 operation), a Q-switch 36, plate polarizers 38, and a high-reflector (HR) mirror 40, which are arranged in a folded or linear configuration, for example. In this configuration, there are two (2) gain modules in the amplification stage 32. A 90-degree rotator is inserted between the gain modules 32 to correct for birefringence distortion. If a single gain module is used in the oscillator, birefringence correction can be obtained by inserting a Faraday rotator.

Optionally, an alternative oscillator configuration may employ a quarter-wave plate in front of the HR mirror 40. This allows the Q-switch 36 to be operated without a voltage drop across its crystal before switching.

Pulse width can be controlled by the length of the resonator, reflectivity of the output coupler 30, or by Q-switch 36 timing relative to peak fluorescence of the gain medium, as known to those skilled in the art. Alternatively, a ring oscillator can be employed for pulse width control.

Additionally, by increasing the diameter of the aperture 34, the oscillator can operate multimode. In this mode, the oscillator can emit greater than 1 J of energy when large diameter rods are used. The use of such a power oscillator can reduce the number of amplifier modules employed in the laser system, and therefore reduce the overall system cost.

Referring now to FIG. 3, there is shown another laser oscillator configuration 45, according to another form of the invention. Birefringence distortion of the laser beam that occurs at repetition rates greater than 0.10 Hz during amplification can be corrected by inserting a 90-degree rotator between twin gain modules. FIG. 3, in particular, depicts an illustration of one such 90-degree rotator correction setup in the MOPA configuration.

A first 90° rotator 46 and a second 90° rotator 47 are each inserted between a respective pair of amplifier modules 48-49 and 50-51. A Faraday rotator 52 is used to isolate the oscillator 44 from amplifier modules 48-49, and Faraday rotator 54 is used to isolate oscillator 44 from amplifier modules 50-51. Additional amplifier modules can be used to increase energy output. Another Faraday rotator can be optionally employed at the output of amplifier modules 50-51 in order to eliminate target reflection effects on the oscillator or amplifier gain.

Referring now to FIG. 4, there is shown another laser oscillator configuration 55, according to another form of the invention. A reduction in the number of gain modules (and hence system cost) can be achieved by double or quadruple passing amplifier modules, although it should be considered that the invention encompasses any multi-pass arrangement. Multiple passes enable the maximum gain to be extracted from a common single set of amplifier modules. FIG. 4 depicts one illustrative multi-pass configuration employing a double-passing arrangement.

In FIG. 4, the multi-pass setup 55 includes a quarter wave plate 56 and an HR mirror 57 that are used to rotate and double pass the emitted laser beam from oscillator 44. A polarizer 58 is used to extract the laser beam before it can pass back into oscillator 44. Another option is to replace the HR mirror 57 with a phase conjugate mirror such as a Stimulated Brillouin Scattering (SBS) mirror. Phase conjugate mirrors will correct for phase distortions caused by thermal effects with the amplifier modules and assist in maintaining alignment of the beam through the amplifier modules.

Various advantages accrue from the laser embodiments shown in FIGS. 2-4. For example, a laser bond inspection system employing aspects of such oscillator configurations will have the following advantageous features: the use of a laser to produce a shockwave for bond inspection; multiple passing for reducing the number of amplifier modules and PFNs; phase conjugation to reduce thermal distortions in the gain medium; multiple Faraday isolators to prevent pulse width variation; variable control of the laser pulse width to control duration of the shockwave; and variable control of the energy to control strength of the shockwave.

Alternative features may involve replacement of the glass gain medium by YAG, YLF, or other solid-state crystal material. Another variation is the use of a slab gain medium in place of a rod shape gain medium in amplifier modules. Another form of the invention may involve configuring the laser as a power oscillator containing one or more large diameter laser rods in a resonator that is capable of emitting greater that 50 J in a temporal pulse width greater than 200 ns.

Referring now to FIG. 5, there is shown another laser oscillator configuration 60, according to another form of the invention.

As one exemplary specification, it was desired to achieve laser pulse widths up to 300 ns to effectively implement the laser bond inspection process. An exemplary repetition rate of 0.125 Hz was employed. For implementation purposes, for example, the required maximum pulse width of 300 ns was obtained by lengthening the oscillator cavity to 2.1 meters, and by changing the radius of curvature of the back mirror to 10 meters. Pulse widths in the range of 70-300 ns were achieved by varying the time the Q-switch was triggered relative to the firing of the oscillator's flashlamps.

A Faraday rotator 61 was used to protect the oscillator from target interaction or amplified spontaneous emission. The exemplary requirement of 50 J per pulse was obtained by configuring the laser as a single beam system. The high-reflectivity mirror assembly 62 enabled all of the energy produced by the amplification section 64 to be channeled into the B-amplifier stage 66 and D-amplifier stage 68.

In an operational run of the FIG. 5 apparatus, it was observed that the temporal pulse shape of the laser pulse remained Gaussian and highly stable, although some longitudinal mode beating was noticed which is not expected to have any effect on the interaction with targets. The spatial profile of the beam was found to be very similar to that seen with the shorter laser pulse, i.e., flat-top with slightly higher irradiance near the center of the beam. Pulse-to-pulse energy stability was also equivalent to that seen with the shorter pulse (±0.5 percent). By making adjustments in pump head voltages and flashlamp timing, the FIG. 5 laser arrangement could be operated with pulses as short as 80 ns. This indicated that any pulse width in the 80 to 300 ns range can be obtained with a laser system constructed according to FIG. 5.

Figure 6:
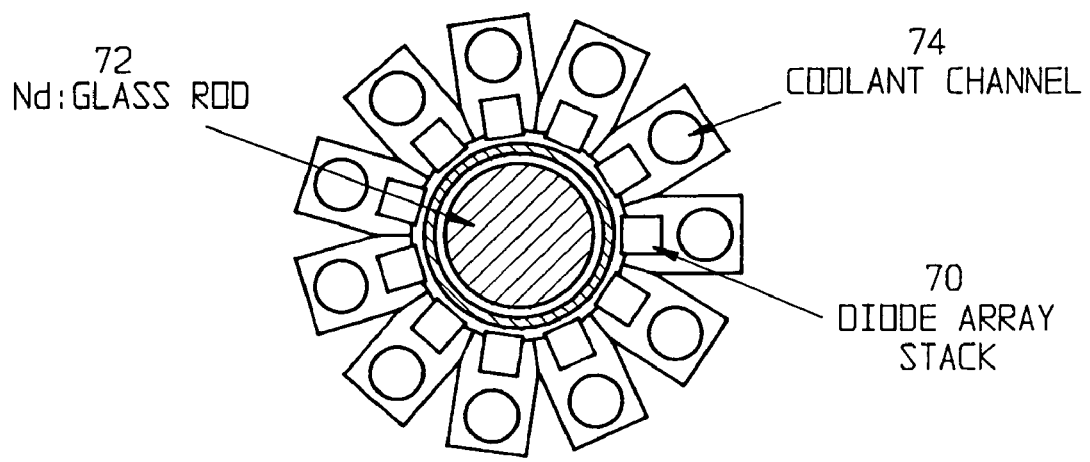
FIG. 6 is an axial cross-sectional schematic view of a diode-pumped cavity for use in a laser design, according to another form of the invention.

Referring now to FIG. 6, there is shown an axial cross-sectional schematic view of a diode-pumped cavity for a laser structure, according to another form of the invention.

Generally, energy can be supplied to the gain medium of the various oscillator configurations by flash lamps, diodes, or any other suitable device. In the case of flash lamps, specular or diffuse reflectors can be used to couple the flash lamp energy into the gain medium. However, diode pumping advantageously does not require reflectors.

In the FIG. 6 setup for a diode-pumped cavity, the diodes 70 can be arranged around the circumference of the gain medium 72 (e.g., Nd:glass rod) or set up for end-pumping the gain medium. The laser rod 72 is preferably contained within a flow tube assembly having coolant channels 74 that enable the rod to be water-cooled.

Diode pumping offers the following advantages over flash lamp pumping:

- the ratio of heat deposited to energy stored in the gain medium is a factor of 3 lower, and
- the waste heat is reduced by a factor of 5, therefore reducing the thermal management requirements and birefringence distortion. These factors enable the laser to be operated at higher repetition rates.

Referring again briefly to FIG. 1, beam delivery system 16 is responsible for transporting the radiant energy generated by laser assembly 14 to process head 18 where the laser emission is directed to article 12 for laser bond inspection.

According to one form of the invention, beam delivery system 16 is implemented with an articulated arm assembly fitted with suitable mechanisms to direct and transport the laser beam.

Implementation of the laser bond inspection process in a practical application such as inspection of an aerospace bonded composite structure typically confronts the designer with difficult and complex geometries in terms of accessing the desired inspection site. Generally, it is necessary to transport the laser beam from the laser beam generator (laser device) to the inspection point on the structure in a precise, reliable, and reproducible manner.

In one configuration of the invention, there is provided an articulated arm laser beam delivery system that has one end fixed relative to the laser. The fixed end of the arm receives the laser beam from the laser device. Mirrors are arranged inside the arm at joints connecting straight sections of the arm. Each mirror turns the beam 90 degrees to a direction parallel with the axis of rotation of the joint. In one exemplary arrangement, seven such joints permit complete freedom of motion to locate the output end of the arm in any orientation to access an inspection point on a test article within reach of the arm. The arm also conveniently serves as a safety enclosure for the laser beam.

One exemplary implementation of the articulated arm beam delivery system may employ an articulated arm such as that manufactured by Laser Mechanisms, Inc. In one illustrative configuration, the arm receives a collimated 27-mm diameter laser beam from the laser assembly 14 and delivers it to process head 18 coupled to the output end of the arm. The arm has seven joints ("knuckles") that allow an operator to move the process head over the workpiece in a variety of orientations. Custom mirrors with high damage threshold fluence are installed in the arm knuckles.

It should be apparent that any suitable mechanism may be used to facilitate transport of the laser emission to the workpiece or article under inspection. Additionally, any form of articulated arm assembly may be used, other than the specific embodiment discussed above.

In general, it is advantageous to use a flexible and selectively configurable and maneuverable delivery system to accommodate different access paths for guiding the laser beam to the target, depending upon the inspection environment. Other features of such a system include the ability to remotely generate and deliver the laser beam to the target. Certain inspection environments will require serpentine-like propagation paths in order to access the target, thereby requiring a delivery system capable of achieving the appropriate beam routing. Additionally, some applications will not accommodate a direct line-of-sight propagation path for the beam travel. Accordingly, the beam delivery system will also be able to effectuate direct and indirect beam communications between the laser and target.

In an alternative beam delivery setup, a fiber optic beam delivery system may optionally be used, provided that the fiber system can transmit the required energy without damage of the fiber. Suitable hollow fibers may be used in this implementation. In one exemplary form, a fiber optic delivery system may include a single fiber or a multiplicity of fibers that could bend in a manner that would allow delivery of the beam energy to an inspection point on a complex structure.

For example, conventional silica fibers are capable of delivering up to about 200 mJ per fiber (for a 1.5 mm diameter fiber) in a 20-ns wide pulse without damage (up to 600 mJ estimated for 300-ns pulses). These fibers are fairly stiff and a large number of them would be required for a multi-Joule system.

Additionally, the beam delivery function may be optionally performed with a set of mirrors arranged on a mechanical gantry system.

Referring again to FIG. 1, process head 18 is provided in one form to facilitate the interface between the output end of beam delivery system 16 and the bonded article 12 under inspection. In general, an important feature of implementing the laser bond inspection process of the invention, or any other process requiring that shockwaves or stress waves be imparted to a workpiece, involves providing a suitable means for transferring the beam from the beam delivery system to the workpiece surface, providing a transparent confining layer, and sensing the results of the process.

In particular, to implement laser bond inspection, the raw beam out of the articulated arm (e.g., 25-mm diameter) must be concentrated and delivered to the work surface to be inspected. A transparent confining overlay should also be applied to the surface before the laser is fired. For example, it was discovered that water overlays served as a practical approach. The water is inexpensive, easy to apply, and entails a minimum of post-inspection cleanup. Transparent solid materials (packing tape, glass, etc.) may also be used but are not as favorable in terms of cost, debris management, and clean-up.

Figure 9:
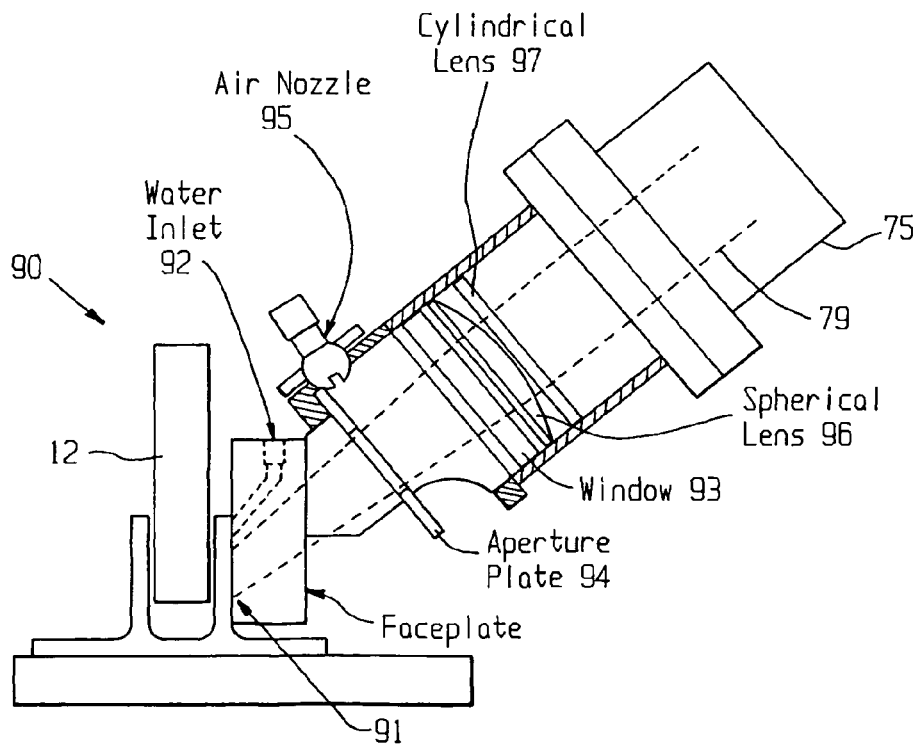
FIG. 9 is a schematic diagrammatic view of another process head attachment employing a water film overlay, according to another form of the invention.

Two process head attachments for the articulated arm were employed to shape the laser beam, provide the water overlay, aid in positioning the head, and house process sensors. In particular, FIG. 7 relates to a water column type overlay design, while FIG. 9 relates to a water film type overlay design. It should be apparent, however, that FIGS. 7-9 depict illustrative arrangements and should not be considered in limitation of the invention, as other suitable process head configurations and overlay designs may be used.

Figure 7:
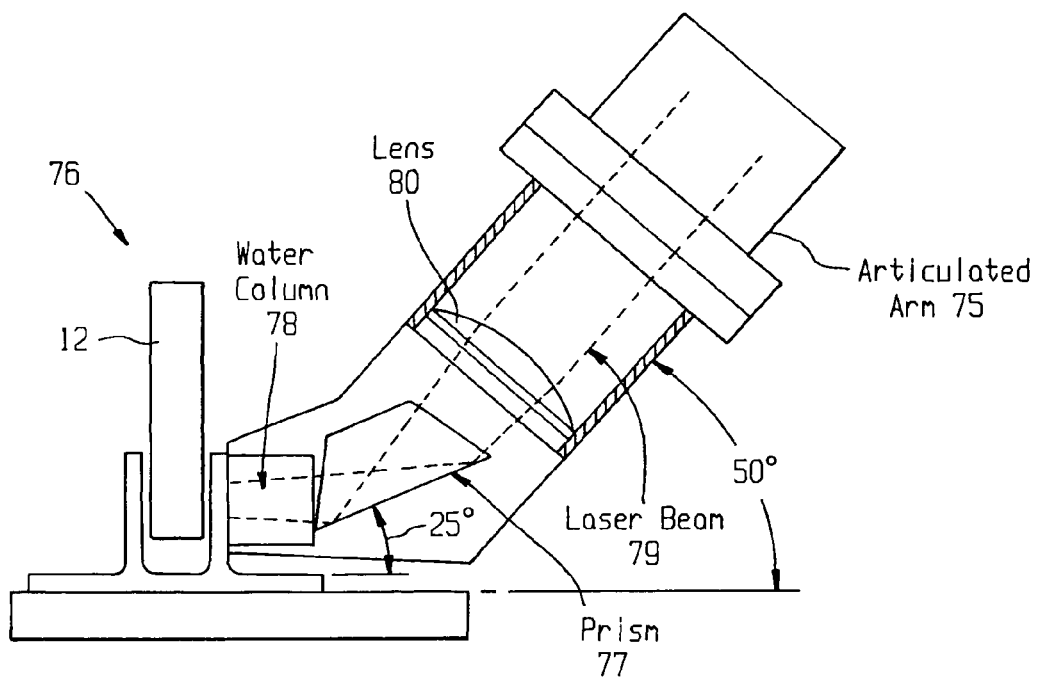
FIG. 7 is a schematic diagrammatic view of one process head attachment employing a water column overlay, according to another form of the invention.

Referring to FIG. 7, there is shown a schematic diagrammatic view of a process head attachment 76 that facilitates delivery of beam 79 from articulated arm 75 (sectional view) to article 12 using a total internal reflection prism 77 and illustrative water column overlay 78.

The design of process head attachment 76 provides a water column type overlay which would have the advantages of confining the stray laser beam reflections, minimizing shock wave concentrations in the optics, eliminating laser-interaction debris deposition on the optics, and providing a circular interaction area for a nearly 45-degree beam axis orientation relative to the surface to be inspected. The latter is important for accessing inside corners in box-like structures.

As shown, in one exemplary form, the water column head design uses a truncated equilateral prism 77 to fold the beam so that a high wall standoff angle can be achieved. The higher standoff angle is important to clearing ribs that may be near a joint in a structure to be inspected. The prism, used in a total internal reflection (TIR) mode, accommodates a high standoff angle (e.g., greater than 30 degrees) without beam profile distortion.

In one exemplary construction, if the prism were tilted at 30 degrees with the horizontal and the input axis were tilted at 60 degrees, the beam incident and exit angles would be normal to the faces of the prism. In this case, the standoff angle would be 30 degrees on one side of the joint and 60 degrees on the other. To minimize beam reflections tracing back to the laser, most flat optical surfaces are usually given a slight tilt. Placing the prism at an angle of 25 degrees with the horizontal (and the beam axis at 50 degrees) avoids back reflections and at the same time adjusts the standoff angle on both sides of the joint closer to the optimum angle of 45 degrees.

An alternative design would employ a mirror in place of the prism and a window to confine the water column. The focusing lens 80 could be placed before the mirror as in the geometry of FIG. 7 or it could be placed after the mirror (adjacent to the window) with a shorter focal length. The latter placement would allow use of a shorter water column and, therefore, would exhibit less beam energy loss. The water column 78 should typically be long in order to maximize the beam area on the prism output face to minimize the potential for laser damage of the prism. A shorter focal length lens (small f-number) placed close to the window confining the water column permits a shorter water column because of the faster convergence of the beam.

Advantages of a water column process head include:
1. Positive Pressure on Absorbing Overlay. Some overlay concepts may employ an absorber in tape form with no adhesive. In this case, the liquid pressure in the cavity will hold the overlay against the substrate to be processed.
2. Debris Management. In the case of thin layer liquid overlays, the liquid splashes back toward the beam delivery optics requiring an air jet to keep the optics clear. For the flooded cavity geometry, there is no splash back and any absorber debris from the absorbing layer is carried away by the water. Overpressure generated in the liquid can be managed by optional stress relief diaphragms or holes (not shown).
3. Gravity Independent. When using a nozzle to produce a thin liquid overlay, the direction of the liquid stream relative to gravity has a significant impact on the layer geometry and uniformity. With the flooded cavity, the liquid overlay is always there and unaffected by gravity regardless of process head orientation on the workpiece.
4. Reliability. With thin layer liquid overlays, there is always a concern as to whether or not the layer is sufficiently thick. For the flooded cavity, there is positive evidence of sufficient liquid, i.e., flow from the liquid exit channel.
5. Laser Beam Reflection Management. For processing with a thin liquid overlay, there is an occasional reflection from the liquid surface that feeds back to the laser and causes a low pulse energy. This problem is particularly acute with short focal length optics, which are required for the articulated arm. In the flooded cavity concept, all reflections are correctly managed by design and no random loss of pulse energy will occur.

The flooded cavity design is particularly useful when laser shock processing is utilized to impart shockwaves to the article. In laser shock processing, the laser pulse interacts with an absorbing layer confined by a transparent overlay. For purposes of providing such confinement, the water column overlay may be employed successfully.

It should be apparent that the design values and parameters associated with the construction of process head attachment 76 are for illustrative purposes only and should not be construed in limitation of the invention, as other specifications are possible within the knowledge of one skilled in the art.

Referring now to FIGS. 8A-C, there is shown a front view, side view, and upper view, respectively, of an illustrative faceplate design 82 for use in the process head attachment 76 of FIG. 7. This construction should not be construed in limitation of the invention, as other designs may be possible.

The faceplate 82 facilitates alignment of the process head to the work surface of article 12. The faceplate includes an outer "O"-ring groove 83 and an "O"-ring around the water column 78, which provide an area that may be evacuated prior to a laser pulse to secure and hold the faceplate firmly against the work surface. The exclusion of water from this region during the pulse will also protect any sensors from stress wave damage and should give improved consistency in the signals from sensors placed in the faceplate for sensing bond integrity and strength.

After the faceplate is seated on the work surface, water is introduced to flood the water column. After a visual check that water is flowing from all drain holes, the laser may be fired. In one design, the faceplate may be released from the work surface and the surface would be flooded to provide good coupling for an ultrasonic (UT) sensor. The faceplate would then be moved to an index mark to place the UT sensor over the laser interrogated spot for confirmation of bond status.

Faceplate 82 is provided with illustrative water inlet 84 and water outlet 85 to facilitate cavity flooding. As discussed further, the process head attachment preferably includes a sensor apparatus for detecting stress wave signatures emanating from the article due to laser interrogation. In one form, the sensor is housed in faceplate 82. For example, as discussed further, an electromagnetic acoustic transducer (EMAT) may be installed in EMAT bay 86 for use in providing sensing functions concurrent with the laser interrogation, while a UT sensor may be installed in UT sensor bay 87 (for use in post-lasing sensing operations, for example).

Referring now to FIG. 9, there is shown a schematic diagrammatic view of a process head attachment 90 that facilitates delivery of beam 79 from articulated arm 75 (sectional view) to article 12 using a water film overlay (generally depicted at 91).

By way of comparison, the water column design of FIG. 7 can deliver surface fluences in the 15-20 J/cm$^2$ range, for example. This is quite adequate for many bond inspection tasks, where the inspection fluence may be 10 J/cm$^2$ or less. Additionally, shortening the water column can further increase the available surface fluence. For some inspection tasks, however, such as thick multi-layer joints or structures with thick attenuating layers of epoxy, greater fluence requirements are present. A process head attachment employing a water film design satisfies such requirements.

In FIG. 9, the beam 79 is directed straight out of the articulated arm 75, through a focusing lens 96, and directly onto the work surface at a 40 degree incidence angle, for example, although other incidence angles are possible by suitable adjustment of the apparatus. The water overlay 91 is provided by a water nozzle entering through inlet 92, which produces a water film with thickness of about 0.5 mm, for example. An AR-coated window 93 protects the lens from water splash and absorbing overlay debris. The water splash is minimized by an air jet (via nozzle 95) directed over an aperture plate 94 that blocks most of the water droplets ejected from the interaction zone.

An optional cylindrical lens 97 may be added to the optical train to produce a circular spot on the work surface. Without the cylindrical lens, the beam spot on the surface is elliptical. However, any beam shape known to those skilled in the art may be used to practice the invention.

It should be apparent that the design values and parameters associated with the construction of process head attachment 90 are for illustrative purposes only and should not be construed in limitation of the invention, as other specifications are possible within the knowledge of one skilled in the art.

The process head constructions disclosed herein include other features as well (not shown). In operation, the operator or a robot arm will position the process head over the area to be processed. If a vacuum system is used, this will pull the head onto the surface and clear water from the sensor area. When the head is in full contact with the surface, water will fill the water column (or issue from the water nozzle in the water film case), and laser firing will be enabled. The operator will then initiate laser firing and sensors in the head will assess the strength of the stress wave and the presence of any flaws produced. As discussed below, sensors in the head may include VISAR probes, EMAT coils, capacitance probes, or piezoelectric ultrasonic transducers.

Referring again to FIG. 1, a sensor assembly is provided in process head 18 to facilitate the collection of laser bond inspection data indicating the integrity of the bond in article 12. In particular, the sensor assembly detects signature data indicative of the stress wave activity present in and/or emanating from the article, such as the stress wave activity induced by shockwave activity arising from laser shock peening treatment.

By way of overview, an important aspect of the laser bond inspection process involves determining when a substandard bond in a structure has been broken by a stress wave generated by the laser pulse. For example, surface motion can indicate the breaking of a bond during the process of stress wave propagation (real-time sensing). Surface motion may also locate a broken bond during a probing stress wave applied after the bond breaking stress wave. The sensing of bond failure in real time will be an important benefit for the inspection process because it could ultimately minimize the need for post-inspection monitoring, such as manual UT scanning.

In one form, the sensing function of the invention may be practiced by employing any of various suitable methods of sensing surface motion, including, but not limited to, non-contact methods such as interferometry, electromagnetic sensing, electrostatic sensing, and optical beam deflection; and contact methods of sensing surface motion such as piezoelectric sensing and current generation in a magnetic field.

For example, a velocity interferometer for surfaces of any reflectance (VISAR) can successfully sense surface motion for purposes of laser bond inspection. However, this instrument is fairly complex and commercial devices are very expensive. According to an advantageous feature of the invention, the sensor apparatus is implemented with an electromagnetic acoustic transducer (EMAT) gauge, which is a very simple and low-cost alternative. In particular, as discussed further, two different embodiments may be used, namely, a non-contact gauge using a pickup coil and a surface mounted gauge that requires electrical contacts (direct-read gauge).

Back-surface on-axis VISAR probing has been demonstrated to be effective in recording bond failure signatures routinely in coupon tests and in limited structure tests. The two types of EMAT gauge mentioned above (pickup coil and direct read) produce signatures having a wave differentiation capability comparable to that provided by VISAR techniques. If the back surface of a joint is accessible, real-time bond failure sensing may be implemented via appropriate engineering known to those skilled in the art.

However, a more favorable design employs front surface sensing with probes housed in the faceplate of the process head. It should be understood that the invention encompasses sensor techniques employing on-axis and/or off-axis sensing at the front surface and/or back surface or any combination thereof.

Figure 10:
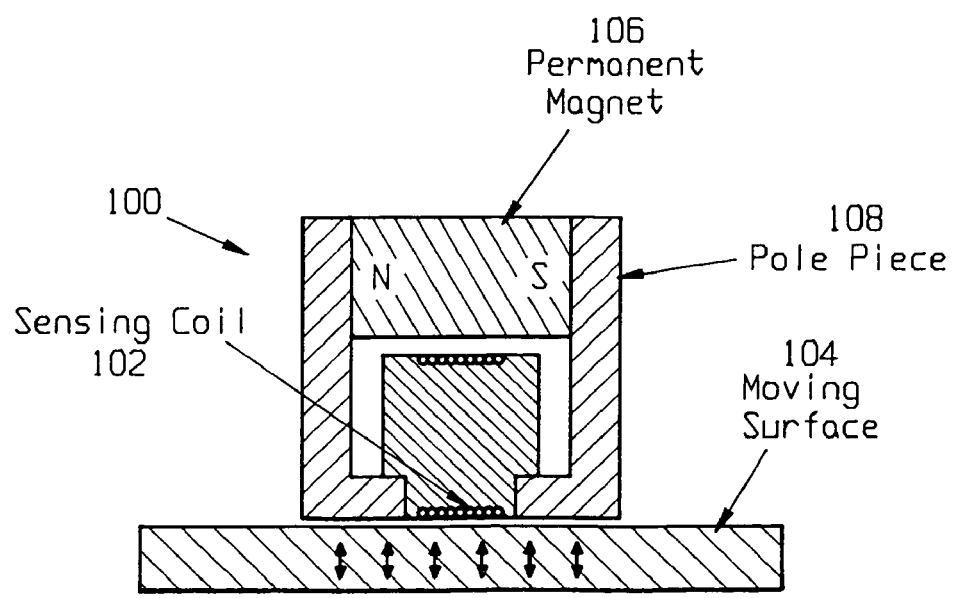
FIG. 10 a cross-sectional diagrammatic view of a non-contact EMAT sensing arrangement, according to one form of the invention.

Referring now to FIG. 10, there is shown a cross-sectional diagrammatic view of a non-contact EMAT sensing arrangement, according to one form of the invention.

The illustrated EMAT gauge 100 includes a sensing coil 102 with portions of the coil adjacent to the surface 104 for which motion is to be sensed. A constant magnetic field is applied (by magnet 106) transverse to the direction of the coil windings that are adjacent to the surface. The magnetic field may be produced in any conventional way, however, permanent magnets, such as NdFeB rare earth magnets, are convenient for this purpose. Pole pieces may be included in the design to concentrate the magnetic field near the moving surface.

The surface 104 must be an electrical conducting surface or have a thin conducting layer such as adhesive backed aluminum foil applied to it. When the surface 104 moves rapidly in the constant magnetic field created by the magnet 106 and pole pieces 108, a surface current is induced in the conducting surface proportional to the magnetic field intensity and the velocity of the surface in a direction perpendicular to the surface. The direction of the induced current is mutually perpendicular to the magnetic field direction and the surface motion in accordance with well-established laws of physics.

This changing current, in turn, induces an electromotive force (EMF) in the coil windings that is proportional to the rate of change of the surface current. A coil signal is read by attaching the coil leads to a coaxial cable (or triaxial cable for noise immunity), for example, and detecting the output of the cable with an oscilloscope or other voltage transient reading device. Typically the cable impedance is 50 ohms and the cable is terminated at the oscilloscope in 50 ohms. By selecting the coil and cable parameters appropriately, the signal is integrated intrinsically with reasonable fidelity for the transient times of interest (typically 1 μs). This leads to the result that the detected signal is reasonably proportional to the surface velocity. In any event, the fidelity is sufficient to find defective bonds by changes in the velocity signature due to reflections at broken bond interfaces.

Figure 11:
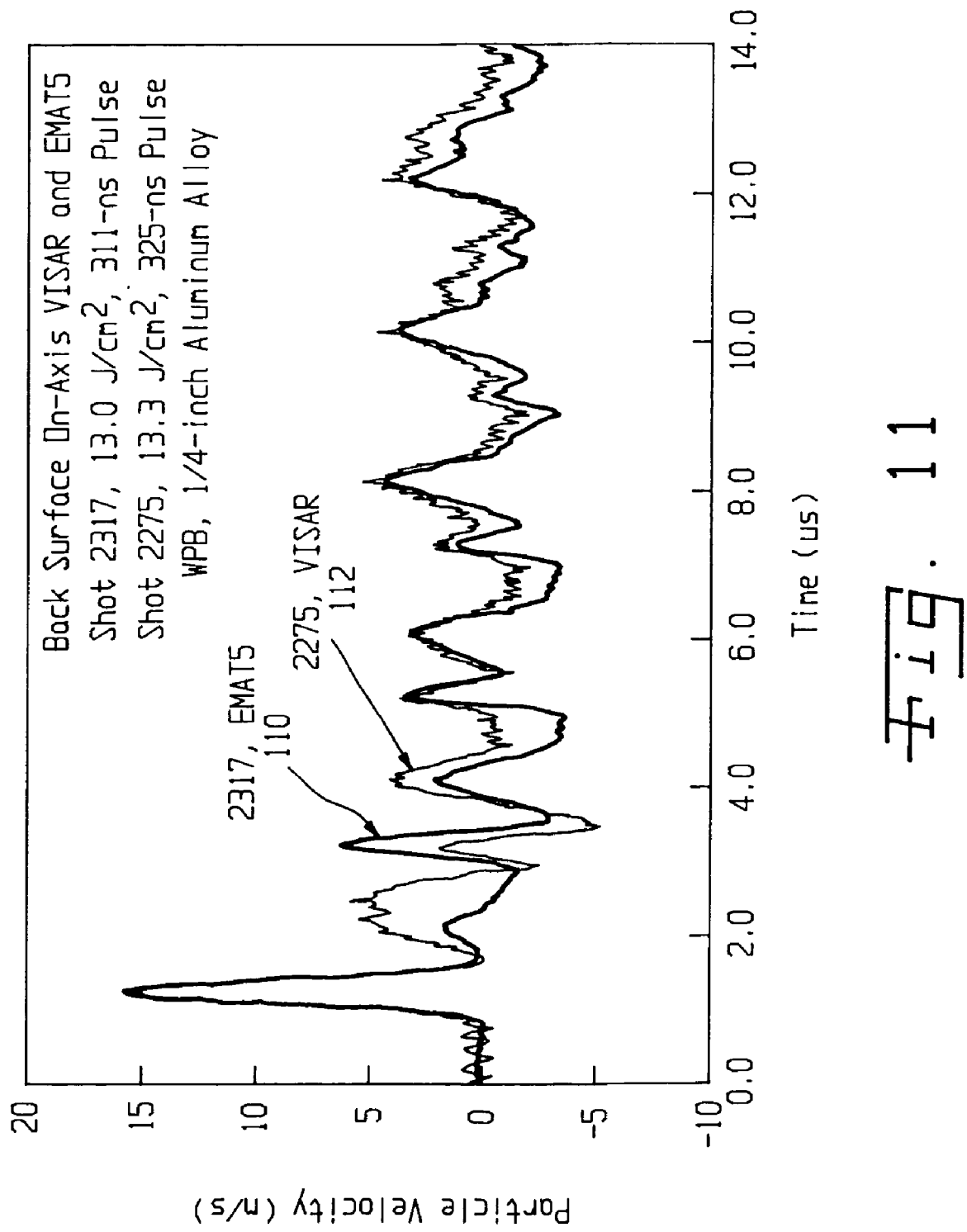
FIG. 11 is a graphical comparison of stress wave signatures measured by a VISAR instrument and a non-contact EMAT gauge constructed in accordance with the design of FIG. 10.

FIG. 11 provides a graphical comparison of stress wave signatures measured by a VISAR instrument and a non-contact EMAT gauge constructed according to FIG. 10. In particular, FIG. 11 compares the on-axis back-surface velocity records provided by non-contact EMAT and VISAR sensors, according to a laser bond inspection process of the invention.

Referring to FIG. 11, curve 110 depicts an EMAT signal taken on-axis on the back surface of an aluminum sample subjected to 13 J/cm$^2$ (300-ns pulse) with a water and black paint overlay, while curve 112 shows a VISAR record for a similar test. Several stress wave signature features are evident. For the first 1.6 μs the signals are nearly identical. Subsequently, there is a period where the signals diverge due to the fact that the VISAR senses an area 1 mm in diameter and the EMAT averages over a larger 3-mm by 5-mm rectangular area in this case. Measurements and code simulations have shown that the stress wave varies strongly with distance from the axis so some differences in the records are expected by the averaging effect. Later in time, after radial transients have settled, the records are nearly the same in every detail. Another advantage of the EMAT over the VISAR (beside lower cost) is the superior signal-to-noise characteristic, which is clearly displayed in the particle velocity measurement data of FIG. 11.

Figure 12:
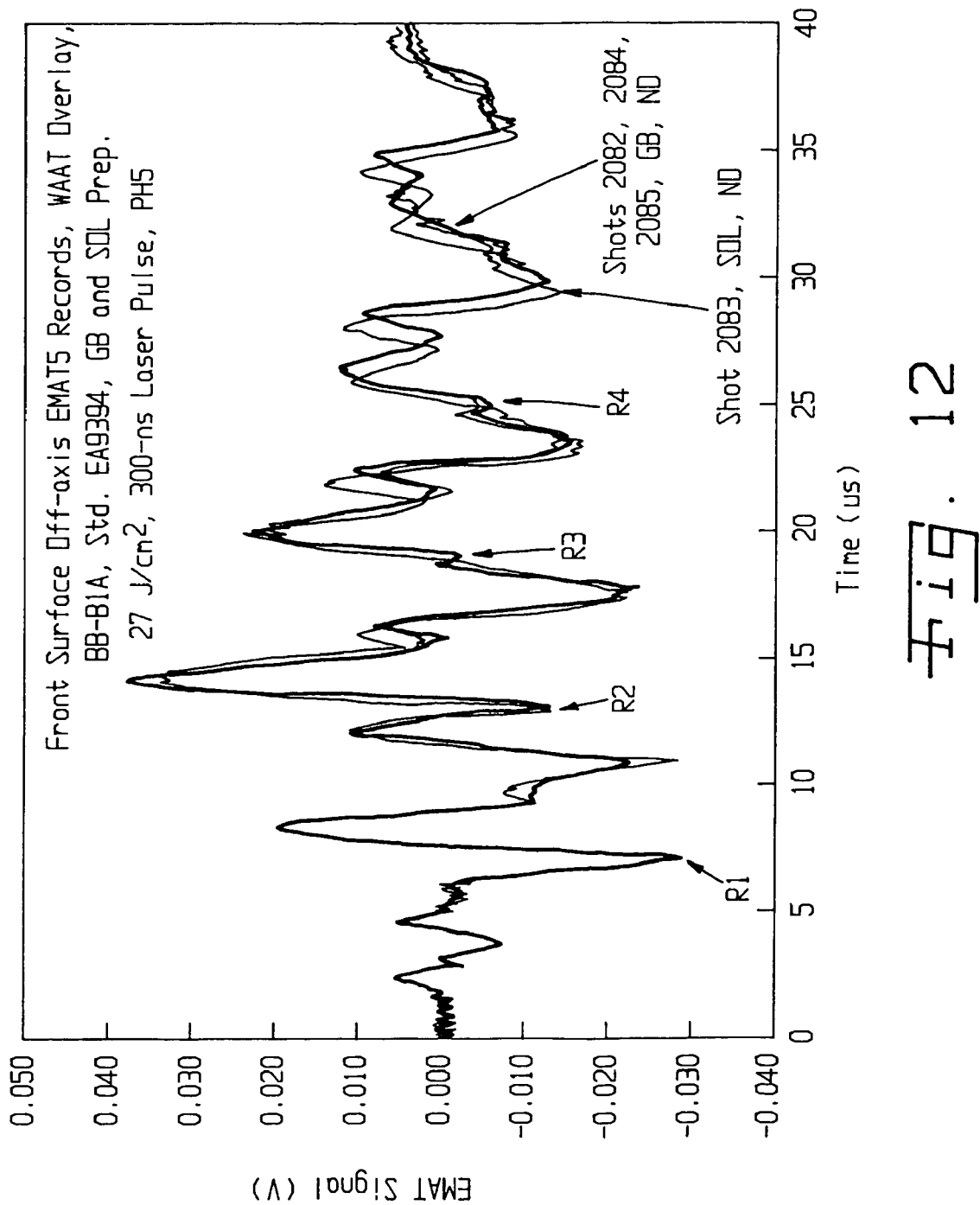
FIG. 12 is a graph of an EMAT stress wave measurement showing a no-damage characteristic profile.
Figure 13:
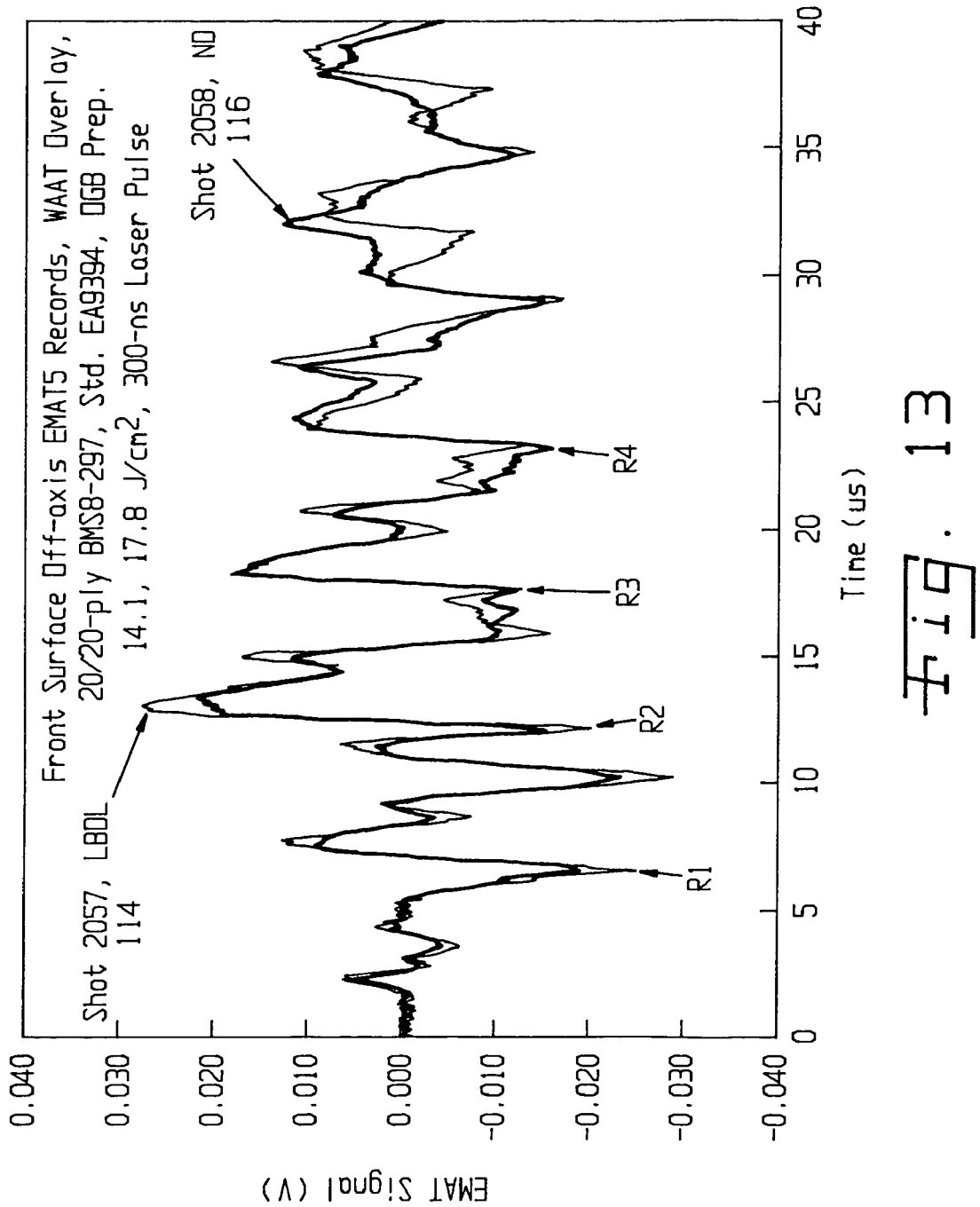
FIG. 13 is a graph of an EMAT stress wave measurement comparing a no-damage profile to a bond failure profile.

FIGS. 12 and 13 show further graphical results of EMAT sensor measurements of stress wave signatures obtained from illustrative laser bond inspection processes.

FIG. 12 show EMAT signatures based on records corresponding to a standard grit blast preparation. An aluminum tape overlay was used. The graph reveals a no-damage condition.

FIG. 13 shows EMAT measurement records obtained from test coupons, using a water film overlay process head. Curve 114 corresponds to a bond failure case, while curve 116 corresponds to a no-damage condition. Curve 114 shows the record for which damage occurred due to the stress wave. In particular, clear deviations of the signature from the no-damage curve 116 are apparent at 32 and 37 µs. These data points are believed to arise from reflections of the propagating stress wave at the broken bond.

The invention may also be practiced with a surface-mounted direct-read EMAT gauge. This gauge construction offers the ability to sense the on-axis front-surface motion directly under the interrogating laser beam spot. In one exemplary direct-read gauge design, a patterned conducting tape is adhered to the surface and the surface current is induced in the patterned conducting tape by the motion of the surface in the magnetic field. Instead of further inducing an EMF in a coil, as above, in this gauge design the current from the patterned conducting tape is connected directly into a cable and the cable is connected to a voltage transient measuring instrument.

An advantage of this approach is that the surface current is read directly and distortions caused by inadequate frequency matching of a pickup coil are absent. The surface current is directly proportional to surface velocity and may be computed from the cable termination resistance at the voltage measuring instrument. Contacts typically need to be applied to the patterned conducting tape to complete the circuit. However, alternately, appropriately designed spring contact pins can be installed in the process head.

The direct-read gauge can be implemented in any of various gauge pattern geometries. For example, illustrative gauge pattern geometries may include on-axis front-surface designs including a 10-mm wide vertical strip, a 5-mm wide vertical strip, a 3-mm wide by 5-mm tall vertical strip with horizontal leads on both sides ("Z" gauge), a 3-mm wide by 5-mm tall vertical strip with horizontal leads on one side ("Pi" gauge), and a 1-mm wide by 5-mm tall Pi gauge. In all cases, the gauges were made of adhesive backed aluminum foil tape (0.002-inch foil, 0.001-inch adhesive). The samples were painted with flat-black paint after placing the gauges on the front surface. Clip leads were used to attach the gauge to a 50-ohm triax cable which was terminated in 50 ohms at the oscilloscope.

One notable on-axis gauge is the pi gauge geometry. The 10-mm and 5-mm wide vertical strip gauges had sensitive areas which covered large areas of the laser spot. For this reason, they averaged over the front-surface signals arriving from broken and unbroken bond areas. The sensitive vertical portion of the pi gauge was localized near the laser beam axis and provided good indications of bond breaks when they occurred.

In comparison to the non-contact EMAT gauge, in the direct read mode of operation, the pickup coil used in the standard EMAT configuration is eliminated in favor of a surface conducting strip which is sensed directly on an oscilloscope. The benefits of this approach include broad bandwidth in surface velocity detection and the potential for direct access to the surface region directly over the bond failure in the case of front surface sensing.

In one demonstration test, a laser bond inspection routine was conducted on the back side of a sample upon which was mounted a 4-mm wide strip of aluminum tape. The vertically-mounted strip was centered on the pulsed laser beam axis and the VISAR beam was centered on the aluminum strip. The magnet assembly (without the pickup coil) was setup in a manner to provide a horizontal magnetic field at the back surface of the sample. The ends of the aluminum strip were connected directly to a coaxial cable which was terminated in 50 ohms at the oscilloscope. This arrangement provides greater fidelity in the measurement of surface velocity because the current measurement is direct, as opposed to the induced coil current normally measured.

Figure 14:
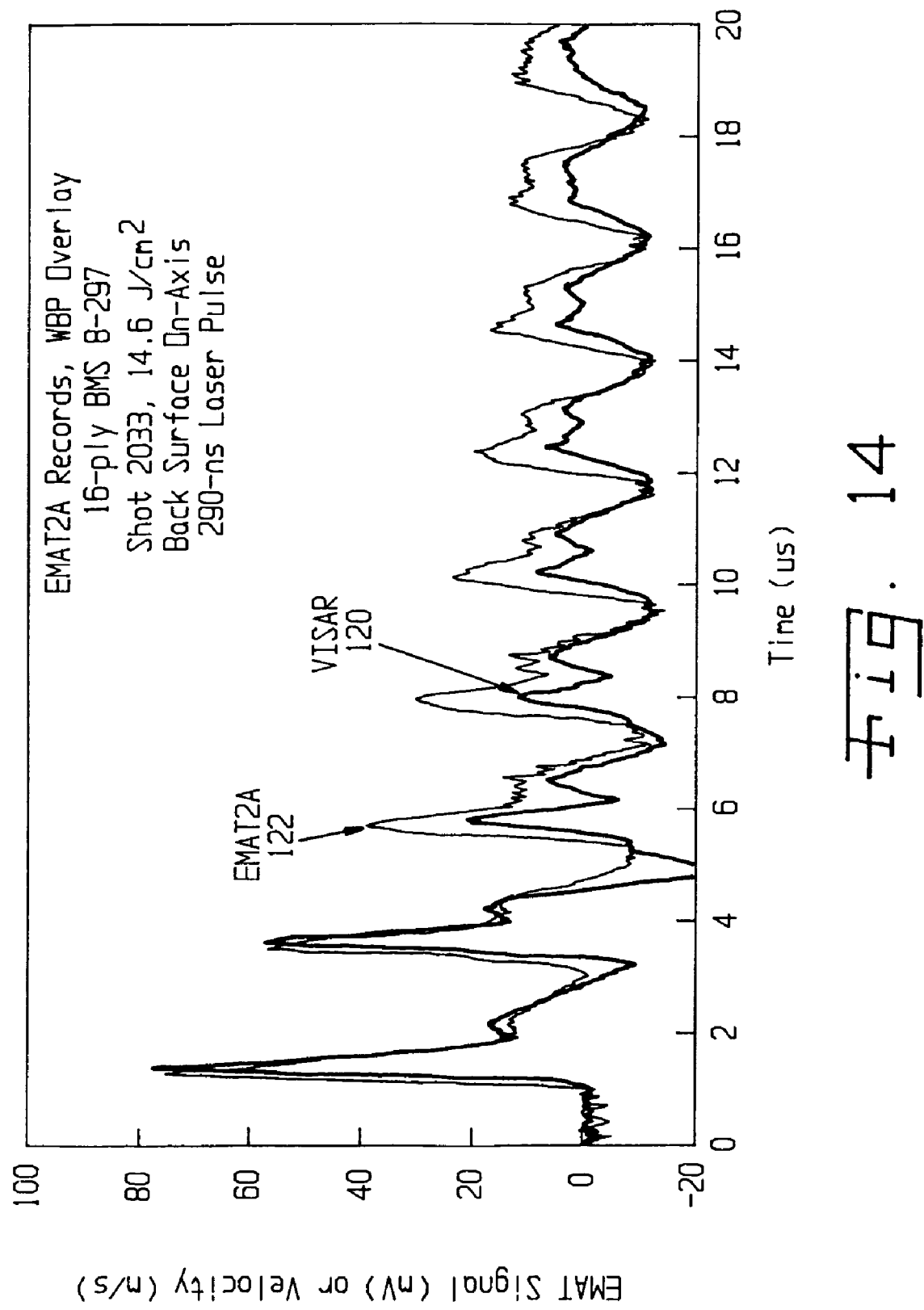
FIG. 14 is a graph comparing sensor measurement records for back-surface VISAR and an EMAT device with surface mounted pickup conductors.

FIG. 14 graphically presents results of simultaneous measurement of back surface velocity with VISAR (curve 120) and the direct read EMAT configuration (curve 122). Even with a relatively weak EMAT magnet, the signal strength is sufficient for the EMAT signal. The agreement between the records is fairly strong even though the EMAT is averaging over the entire width of the projected main laser beam spot area, while the VISAR senses a 1-mm diameter local area near the main beam axis. The slight shift in time between the two signals is due to delays in the VISAR electronics.

Various implementation aspects apparent to those skilled in the art will be associated with construction of a gauge realizing front-surface sensing with an on-axis EMAT. For example, construction details include the appropriate magnet configuration, custom overlays, and an electrical contact system. The manner of incorporating the gauges discussed herein into the process head attachments will also be apparent to those skilled in the art.

The invention may use any suitable type and shape of laser beam interaction spots, such as circular and elliptical. Certain beam shapes, however, are favorable because they accommodate certain sensors for detecting bond failures. If a circular beam has a rectangular region removed from the center, a sensor such as an EMAT coil or a VISAR probe can be placed on the axis of the spot to implement the most favorable geometry for real-time sensing of bond failure, for example, a front-surface mounted "pi"-type EMAT gauge.

Since the center of the beam is available for a non-contact or temporary contact sensor placed in the process head, the problem of contacting a surface mounted sensor is eliminated. One such beneficial beam spot is the "double D" beam shape shown in FIG. 15. In tests, this pattern produced laser-generated stress waves that broke bonds in a bonded composite sample, although the threshold fluence for bond failure was higher than that for a circular beam with the same fluence.

Figure 15:
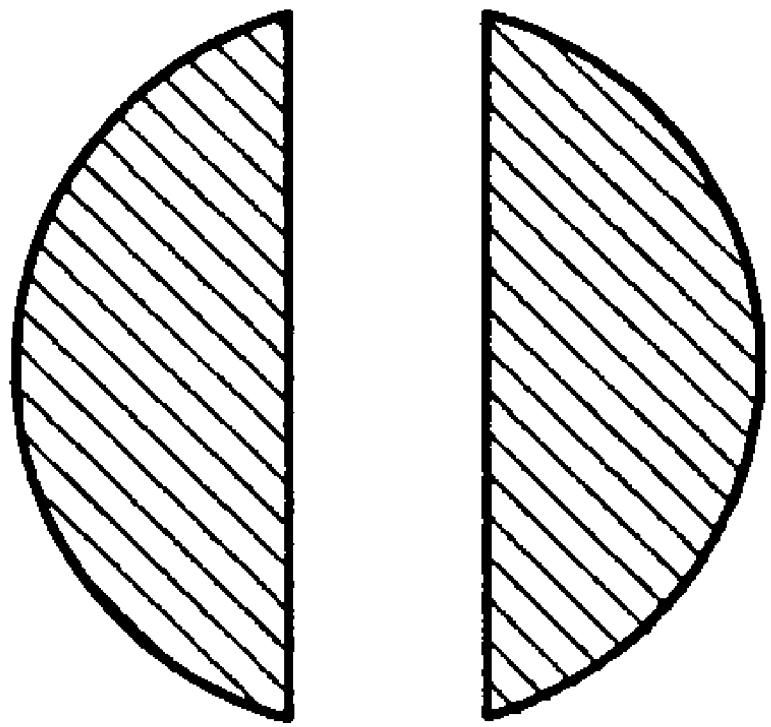
FIG. 15 shows an exemplary double-D beam irradiance patter for use in the invention.

The pattern of FIG. 15 was produced by placing an obscuration in the beam which was wasteful of energy. As an alternative, two parallel ellipses could be formed by conventional optics employing a beam splitter without significant energy loss. A variety of beam shaping optical techniques are available for efficiently forming beams with gaps. These include beam splitting, light guiding, diffractive optical elements, a multiplicity of conventional lenses, or any other conventional device known to those skilled in the art. A multiplicity of optical fibers may also be used to form patterns.

The following tabulation provides an exemplary and illustrative set of specifications and requirements for the system of FIG. 1, but should not be considered in limitation of the invention as other configuration parameters and values may be used.

Laser beam parameters: 50 J per pulse; 70-300 ns pulse width (Gaussian shape); 0.125 Hz pulse repetition rate; flat-top spatial profile at work surface; pulse energy and pulse width stable to ±5%; and 6-10 mm beam diameter at work surface.

Laser packaging: stationary laser housing and power supply; 8×12 ft footprint; and beam enclosed with safety shutters between laser and beam delivery system.

Beam delivery system: articulated arm construction; beam enclosed except at process head; arm counterbalanced for easy manipulation by one operator; process head accessible to open surfaces such as the X-45 UCAV carry-through box; operator-positioned process head; and placement point stable to ±1 mm.

Process head: vacuum hold-down; water film supply; and sensor bays.

Front surface bond failure sensor: EMAT and/or VISAR sensors integral with the process head; multiple point data collection; input stress wave monitor (data extracted from surface wave information); and bond failure alarm to alert operator.

Control system: laser safety interlock system; laser fire control; process sequencer; and data acquisition, analysis, evaluation, processing, and archiving system for pulse energy, pulse width, and front surface sensors.

In the above system, as with other laser bond inspection processes herein, it is possible to employ a laser pulsing operation to interrogate structures such as bonded composite articles for the presence of weakly bonded interfaces. Essentially, the laser pulse interacts with special overlay materials (temporarily placed on the front surface) to produce a pressure pulse in the 0.1 to 5 kbar range, for example. This pulse passes through the composite as a compression wave, reflects from the rear surface as a tensile wave, and fractures any weak bond material or interface. Simultaneous detection of stress wave transients or subsequent inspection of the material with the sensor apparatus discussed herein reveals the presence of the weak bond. For cases where the bond is strong, the method is non-destructive. Many application environments are possible, such as aircraft, aerospace structures, missiles, automotive bodies, sporting good, and building materials. Additionally, any part or structure that is held together in part or whole by adhesive bonding may be studied by the invention.

Further enhancements are possible as well. For example, control switch can be added to the arm output knuckle. The beam delivery system can also be further tailored to access highly confined spaces, such as wing volumes with small access ports. A double-pulsed oscillator is also possible for dual-sided processing of joints.

Other considerations will also be apparent to those skilled in the art in order to tailor the system parameters, such as: the effects of beam size, shape (circular, ellipse, annular, etc.), and edge proximity on stress wave propagation and bond failure behavior; and the effect of laser beam pulse width on the fluence requirement for breaking bonds.

The invention offers the following beneficial features: measurement of stress wave propagation and bond failure behavior in composite and bonding materials of interest; measurement of stress wave propagation and bond failure behavior in joint geometries in structures of interest; measurement of progressive damage characteristics as a function of laser pulse width; and measurement of progressive damage characteristics for new materials and geometries of interest.

In brief, a critical need in the aircraft industry is the on-aircraft-structure non-destructive inspection (NDI) of composite bonds. In particular, it is of interest to find weakly bonded layers in multi-layer carbon-fiber/resin-matrix skins and internal members. These weak bond areas typically are not observable with conventional ultrasound or thermal techniques because the bond between layers, while weak, is intact and no delamination area exists.

However, in the invention, the use of short laser pulses has been demonstrated to be an effective means of generating stress waves for NDI. The process of laser bond inspection (LBI) entails deposition of laser energy at the front surface (which generates a compressive stress wave), propagation of the stress wave to the rear surface, reflection of the compressive stress wave to form a tensile wave, and breaking of weak bonds with the tensile wave. The debonded interface may be detected by conventional ultrasound after the laser exposure or by techniques used simultaneously with the laser exposure (EMAT gauges).

For example, short (20 to 300-ns) laser pulses from a Nd:glass laser could be employed to produce stress waves that would interrogate composite materials and locate weakly bonded interfaces. Several surface overlay structures were found to be useful in generation of stress waves, however a simple water/black paint (WBP) was found also to be an effective approach for bonded composites when used in combination with 300-ns pulses.

Real-time sensing and evaluation of bond failure during the LBI process involves various strategies and tasks, such as identification of those features in the particle velocity signatures relating to the presence of a failed bond and those that may be attributed to the dynamics of bond failure.

A series of tests was conducted to assess the ability to detect bond failure from surface motion measurements. Previous tests have indicated that an on-axis back surface measurement of particle velocity can provide indicators of bond failure in real time. In the present tests, a VISAR probe measured the back surface velocity history in sequences of three tests on a single spot on 20/20-ply BMS 8-297 bonded coupons. The first test was a low fluence pre-probe test to establish a baseline velocity signature for the coupon. The second test on the same area was a pulse designed to break the bond at fluence levels near or well above the threshold fluence for bond failure. The final test on a spot was a post-test probe to interrogate the bond after it had been broken by the second pulse.

Figure 16:
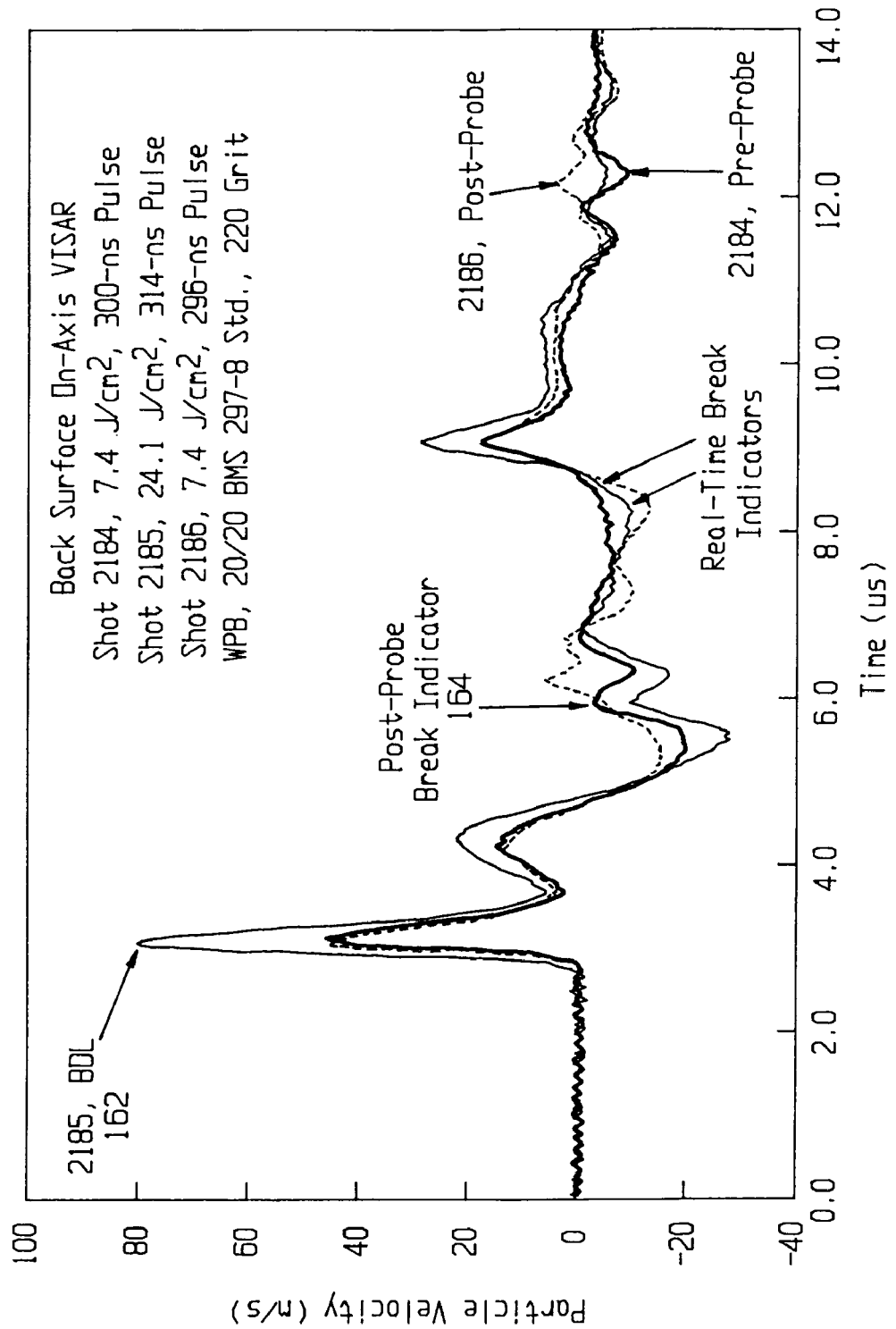
FIG. 16 graphically shows back-surface VISAR signatures for pre-test probe, bond-breaking shot, and post-test probe tests of a bonded article.

FIG. 16 graphically shows typical results from such tests on a single area for a fluence level just above the threshold for bond failure. Curve 162 shows the velocity history for the pulse that broke the bond. The peak at 3 µs is due to the arrival of the compressive wave at the back surface and the secondary hump is due to the beam edge release wave. The double hump at 6 µs results from a weak reflection at the bond line arriving at the back surface. It is conjectured that no indication of bond failure appears at this point because, for a threshold break, the bond fails on the tail end of the pulse.

Two features appear just before the reflection of the main stress appears at the back surface (9 µs). The first feature is a slow dip in the signal, which is followed by the second feature, a sharp inflection in the signal. Viewing trace 162 by itself, these features may not be sufficiently pronounced to use as reliable break indicators.

By using a post-break probe test (trace 164), the bond is clearly identified as broken. The reflection of the probe stress wave at the broken interface is prominent at 6 μs. The dip and inflection indicators are also present and stronger than in the breaking pulse. Another indicator is seen at 12 μs when the third bond-line reflection arrives at the back surface. For the breaking pulse the reflection is sensed as an offset and in the post-probe pulse the reflection is clearly enhanced. The data suggest that threshold bond failures may require probe tests or intensive signal processing to achieve high reliability LBI.

Figure 17:
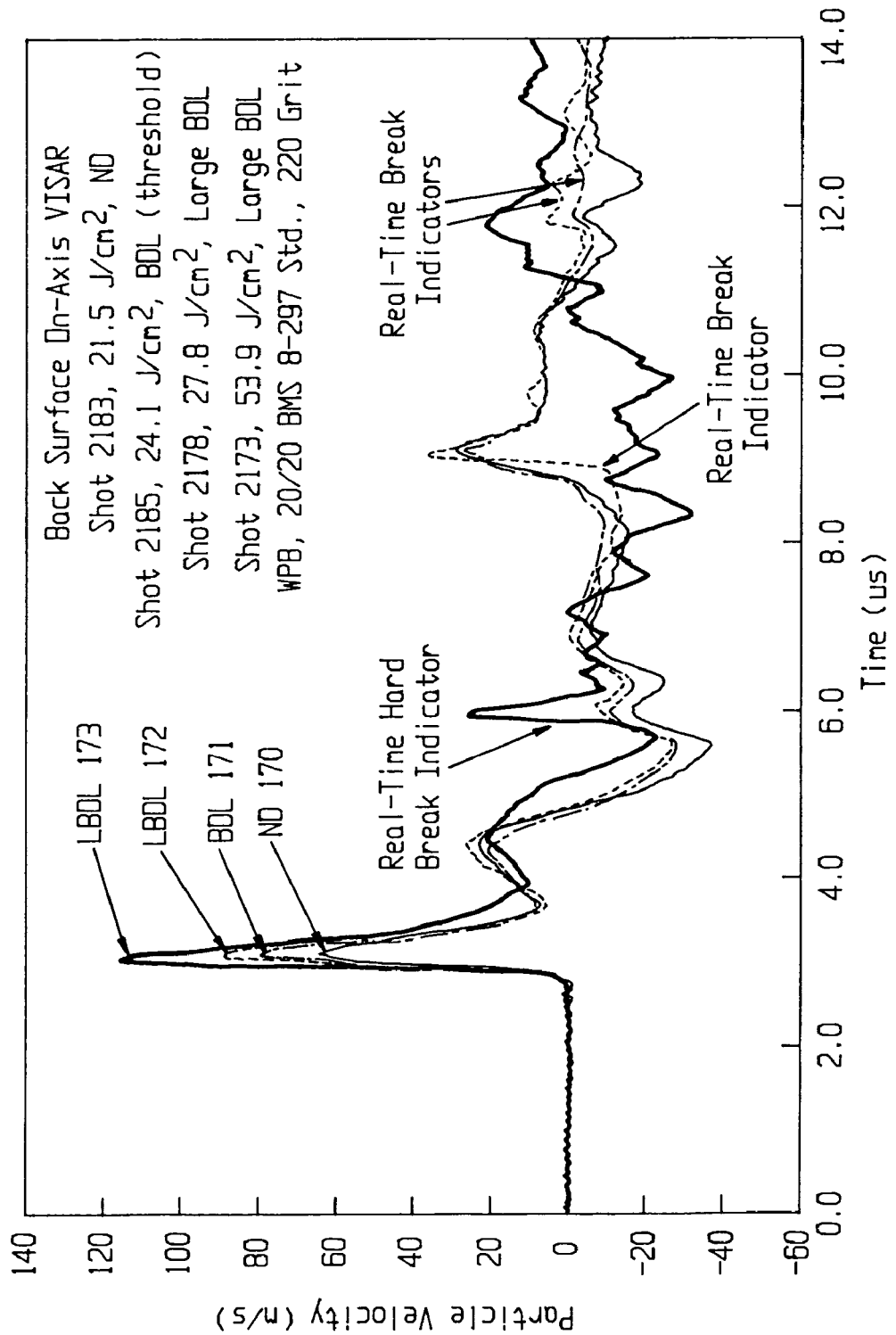
FIG. 17 graphically shows back-surface VISAR signatures of bond-breaking shots on different test areas of a bonded article.

Additional tests were performed with fluences well above the threshold for bond failure to follow the evolution of break indicators. FIG. 17 presents signature data for four tests on different areas. Curve 170 provides a baseline for a no-damage case at a fluence level near the threshold for bond failure. No inflection-type break indicators are evident, although there is a dip at 8 μs. The clean third echo of the bond line at 12 μs is a good indication of no break.

Curve 171 is for a fluence level 15 percent above threshold (taken from FIG. 16). The best dynamic indicator in this case appears to be the offset of the signal at 12 μs. Trace 172 shows the velocity history for a fluence that is 32 percent above the threshold for bond failure. A sharp inflection in the signal at 9 μs and an enhanced reflection at 12 μs indicate bond failure. When the fluence was raised to more than twice the threshold for bond failure (curve 173), the bond broke on the leading edge of the stress wave and a clear reflection from the break is seen at 6 μs.

The basis for most of the break indicators is reasonably well-understood with the exception of those occurring at 9 μs. For the 20/20-ply sample (or any symmetric sample), the second bond line reflection occurs nearly simultaneously with the front surface reflection. This coincidence leads to complex waveforms.

Figure 18:
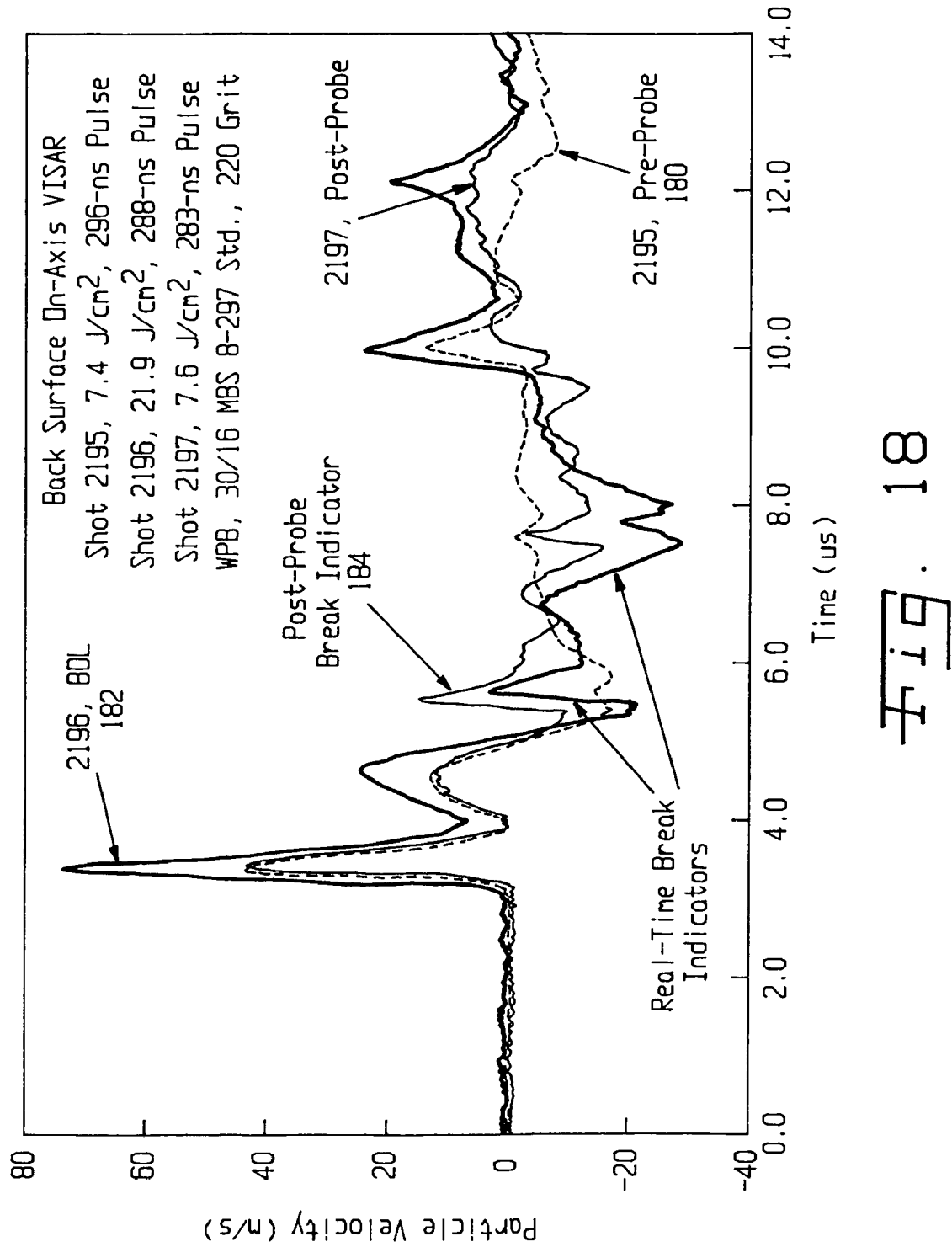
FIG. 18 graphically shows back-surface VISAR signatures for pre-test probe, bond-breaking shot, and post-test probe tests of a bonded article.

A series of tests was conducted with an asymmetric sample to sort out the origin of some of the break indicating features. FIG. 18 presents VISAR signatures for a 30/16-ply BMS 8-297 bonded sample subjected to a probe/break/probe sequence similar to that shown in FIG. 16 for the 20/20-ply sample. Trace 180 shows the pre-test probe signature with small blips at 2.2 μs and 4.4 μs after the main stress wave indicating the first and second bond line reflections. The third bond-line reflection arrives with the first front-surface reflection, however the fourth bond-line is visible at 12.1 μs. An important feature of trace 180 is the negative dip in stress after the second compressive hump. This is the usual characteristic of a stress wave arriving at the back surface through undamaged material.

If the characteristic double hump followed by a negative dip were to be reflected from a damaged bond, then this would explain the negative-dip bond-break indicator seen in FIG. 16. This effect is particularly evident in the curve 182. In this test, the bond apparently broke on the leading edge of the main tensile wave. The curve trace 182 between 5.5 μs and 7.5 μs replicates the characteristic double hump followed by a negative dip which is the reflection from the broken bond superimposed on the normal stress wave pattern. If the bond had broken near the tail of the tensile wave, only the dip would be indicative of the break. In the 20/20 case, this dip-type break indicator occurs just before the arrival of the front surface reflection.

The curve trace 184 shows the VISAR signature for the post-test probe shot. A clear indication of a broken bond is indicated by the reflected wave appearing at the back surface at 5.6 μs.

Regarding the use of EMAT sensors as discussed previously, a direct read EMAT design involves, for example, a conducting foil strip placed directly on the back surface of a composite sample. A static magnetic field is imposed transverse to the strip and current produced in the strip by surface motion is read directly on an oscilloscope. Simultaneous VISAR measurements confirmed that the direct-read gauge provided high-fidelity surface velocity signatures. The direct-read gauge provides the opportunity to acquire on-axis front-surface velocity histories.

Several gauge geometries were studied, including a 10-mm wide vertical strip, a 5-mm wide vertical strip, a 3-mm wide by 5-mm tall vertical strip with horizontal leads on both sides ("Z" gauge), a 3-mm wide by 5-mm tall vertical strip with horizontal leads on one side ("Pi" gauge), and a 1-mm wide by 5-mm tall Pi gauge. Several tests were taken with the pi gauge mounted on the front surface of 20/20-ply BMS 8-297 coupons bonded with standard EA9394 adhesive (220 grit blast). Simultaneous back-surface on-axis VISAR measurements were also made during the tests.

Figure 19:
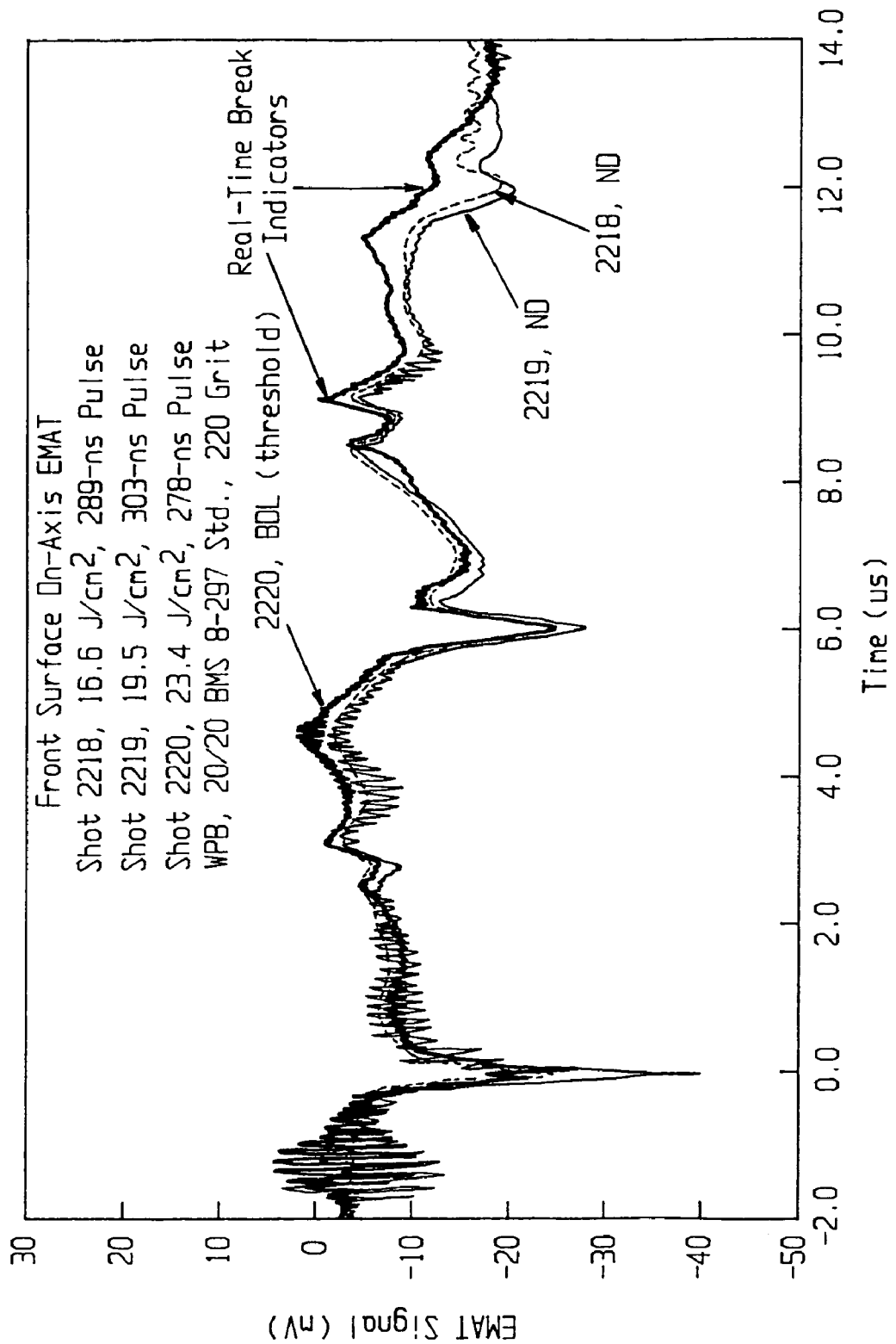
FIG. 19 graphically shows front-surface on-axis direct-read EMAT signals below and at threshold for bond failure.

FIG. 19 presents pi-gauge EMAT records for a sequence of three tests on the same spot with increasing fluence. The sensitive vertical portion of the pi gauge was localized near the laser beam axis and provided good indications of bond breaks when they occurred.

The laser bond inspection process of the invention can also be applied to the detection of so-called "kissing bonds", which generally refers to a surface-to-surface joint contact that is not bonded. A kissing bond is one that has no strength but typically cannot be discovered by conventional inspection such as ultrasonic testing (UT) because the bond interface surfaces may be pressed into good contact by the structure.

Figure 20:
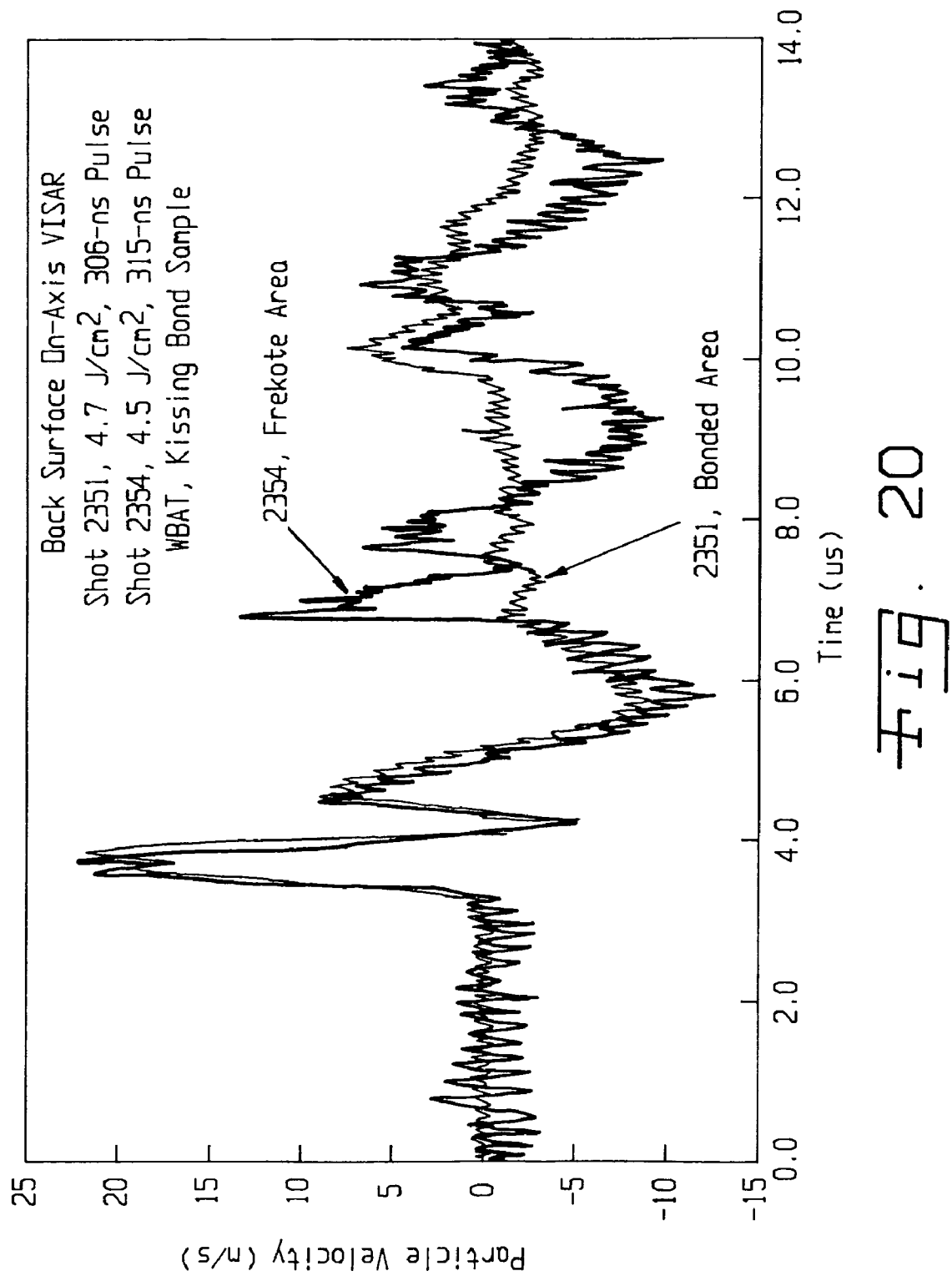
FIG. 20 graphically shows VISAR measurements records for a kissing bond sample.

A kissing bond standard sample tested by the LBI process of the invention permitted the identification of an existing kissing bond. In particular, it was discovered that real-time sensing with an on-axis back-surface VISAR probe clearly distinguished between good bond area and kissing bond area. FIG. 20 graphically depicts the particle velocity measurement records for one of these tests.

The kissing bond area was produced by coating one surface to be bonded with Frekote, a commercial mold release agent. The large deviation in the VISAR signal for the Frekote area at 6.8 μs represents a reflection from the kissing bond. A kissing bond cannot support tension and will give a good dynamic reflection even though the bond gap will close up after the test. This defective bond was not sensed by UT before or after the LBI test.

It is noted that front surface on-axis sensing of surface velocity should also work because the transmission of the tensile wave through the kissing bond will be small compared to that of a good bond. It is clear from the above discussion that low cost EMAT sensors operating on the front or back surface of a sample will find a kissing bond (as well as other defects in bonds that alter the surface motion in response to laser pulses and other sources of rapid surface pressure application).

In one form of the invention, the generation of a stress wave is enhanced by a confining layer that is transparent to the laser wavelength. This confining layer is placed over an opaque layer that absorbs the laser light (which may also be the material itself). This method of generating a stress wave is commonly used in a method of improving materials known as laser-shock processing. Examples and details of laser shock processing treatment may be found in U.S. Pat. Nos. 5,741, 559, 5,911,891, 6,412,331, and 5,131,957, each incorporated herein by reference thereto.

It should be understood that the invention can be practiced to assess the minimum dynamic strength of any material. Accordingly, any material specifications herein should not be considered in limitation of the invention but merely illustrative thereof. Examples of material compositions that may be investigated by the invention include, but are not limited to, armor materials such as ceramics and metal matrix composites. Some specific material types may include, but are not limited to, alumina, silicon carbide, silicon nitride, and boron carbide.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for laser bond inspection of a bond in a bonded article, the method comprising:
    directing a laser beam to a surface of the bonded article to induce generation of stress wave activity in the bonded article, wherein the directing comprises directing the laser beam in a probe-break-probe inspection sequence comprising a first laser pulse having a first fluence, a second laser pulse having a second fluence which is greater than the first fluence but less than a fluence required to break the bond, and a third laser pulse having a fluence which is approximately the same as the first fluence;
    acquiring a stress wave signature indicative of the stress wave activity generated in the bonded article; and
    determining integrity of at least a portion of the bond, using the stress wave signature.

2. The method as recited in claim 1, wherein the directing comprises directing the laser beam using an articulated arm assembly having at least one mirror disposed therein.

3. The method as recited in claim 1, further comprising:
    at least one of: (1) applying a substantially transparent medium to the bonded article; and (2) applying a substantially opaque overlay to the bonded article and providing a substantially transparent medium over the opaque overlay.

4. The method as recited in claim 1, further comprising phase conjugating the laser beam.

5. The method as recited in claim 1, further comprising employing Faraday isolation of the laser beam.

6. The method of claim 1, wherein the generation of stress wave activity comprises the generation of movement of the surface.

7. A system for measuring bond strength in an article containing at least one bond, the system comprising:
    a laser configured to direct a laser beam in a probe-break-probe inspection sequence comprising a first laser pulse having a first fluence, a second laser pulse having a second fluence which is greater than the first fluence but less than a fluence required to break the bond, and a third laser pulse having a fluence which is approximately the same as the first fluence;
    a sensing coil, at least a portion of which is adjacent to at least one of a first surface and a second surface of the article, wherein the sensing coil is configured to detect a stress wave signature indicative of at least a partial failure in a bond; and
    a magnet, capable of applying a magnetic field to at least one of the first surface and the second surface.

8. The system as recited in claim 7, further comprising a processor to determine the bond strength, using the stress wave signature.

9. The system as recited in claim 7, further comprising at least one of:
    an applicator to apply a substantially opaque overlay to the article;
    an applicator to apply a substantially transparent medium to the article; and
    an applicator to provide a substantially transparent medium over the opaque overlay.

10. The system as recited in claim 7, further comprising a controller configured to activate the laser in a pulsing operation.

11. The system as recited in claim 10, the controller being configured further to selectably vary the laser pulse width.

12. The system as recited in claim 7, further comprising a controller to control operation of the laser, the controller being configured further to selectably vary laser beam energy.

13. The system as recited in claim 7, further comprising a phase conjugator operably coupled to the laser.

14. The system as recited in claim 7, further comprising a Faraday isolator operably coupled to the laser.

15. The system of claim 7, wherein at least one of the first surface and the second surface is at least one of electrically conductive and having an electrically conductive layer attached thereto.

16. The system of claim 7, wherein at least one of the first surface and the second surface has an electrically conductive layer attached thereto.

17. The system of claim 7, further comprising an articulated arm assembly configured to direct the laser beam to the article.

18. A system, comprising:
    a laser source configured to induce the generation of stress wave activity in a bonded article via a laser beam having the following parameters: (1) 3-50 Joules per pulse; (2) 70-300 ns pulse width; and (3) 6-10 mm beam diameter at a surface of the bonded article; and
    a sensor configured as a Pi-type EMAT gauge to detect a stress wave signature indicative of the strength of a bond in the bonded article.

19. The system of claim 18, wherein the sensor is configured to detect an off-axis stress wave signature.

20. An apparatus for determining a strength of a bond in a bonded article, the apparatus comprising:
    a laser configured to generate a laser beam, wherein the laser beam has the following parameters: (1) 3-50 Joules per pulse; (2) 70-300 ns pulse width having a Gaussian shape; and (3) 6-10 mm beam diameter at the surface;
    an articulated arm assembly having at least one mirror disposed therein and being configured to direct the laser beam to the bonded article;
    a laser processing head configured to provide an interface between an output of the articulated arm assembly and the bonded article; and
    a sensor to detect a stress wave signature indicative of the strength of the bond in the bonded article.

* * * * *